(12) United States Patent
Klaassen et al.

(10) Patent No.: US 12,012,604 B2
(45) Date of Patent: *Jun. 18, 2024

(54) ACETATE CONSUMING YEAST CELL

(71) Applicant: DANISCO US INC., Palo Alto, CA (US)

(72) Inventors: Paul Klaassen, Echt (NL); Jozef Petrus Johannes Schmitz, Echt (NL); Paulus Petrus De Waal, Echt (NL); Arjen Bouma, Echt (NL)

(73) Assignee: Danisco US Inc., Palo Alto, CA (US)

( * ) Notice: Subject to any disclaimer, the term of this patent is extended or adjusted under 35 U.S.C. 154(b) by 350 days.

This patent is subject to a terminal disclaimer.

(21) Appl. No.: 17/347,204

(22) Filed: Jun. 14, 2021

(65) Prior Publication Data
US 2021/0310013 A1    Oct. 7, 2021

Related U.S. Application Data

(63) Continuation of application No. 15/575,538, filed as application No. PCT/EP2016/061099 on May 18, 2016, now Pat. No. 11,319,543.

(30) Foreign Application Priority Data

May 22, 2015 (EP) .................................... 15168833

(51) Int. Cl.
| C12N 15/81 | (2006.01) |
| C12N 9/00 | (2006.01) |
| C12N 9/02 | (2006.01) |
| C12N 9/04 | (2006.01) |
| C12N 9/12 | (2006.01) |
| C12N 9/16 | (2006.01) |
| C12N 9/92 | (2006.01) |
| C12P 7/06 | (2006.01) |
| C12P 7/10 | (2006.01) |

(52) U.S. Cl.
CPC ........... *C12N 15/81* (2013.01); *C12N 9/0006* (2013.01); *C12N 9/0008* (2013.01); *C12N 9/1205* (2013.01); *C12N 9/16* (2013.01); *C12N 9/92* (2013.01); *C12N 9/93* (2013.01); *C12P 7/06* (2013.01); *C12P 7/10* (2013.01); *C12Y 102/0101* (2013.01); *C12Y 207/01028* (2013.01); *C12Y 207/01029* (2013.01); *C12Y 301/03021* (2013.01); *C12Y 503/01005* (2013.01); *C12Y 602/01001* (2013.01); *C12P 2203/00* (2013.01); *Y02E 50/10* (2013.01)

(58) Field of Classification Search
CPC .... C12P 7/10; C12N 9/0008; C12Y 102/0101
See application file for complete search history.

(56) References Cited

U.S. PATENT DOCUMENTS 11,319,543 B2 * 5/2022 Klaassen ........ C12Y 102/01004

FOREIGN PATENT DOCUMENTS

| WO | 2011/010923 A1 | 1/2011 |
| WO | 2013/081456 A1 | 6/2013 |
| WO | 2014/033019 A1 | 3/2014 |
| WO | 2014/207105 A1 | 12/2014 |
| WO | 2015/028582 A2 | 3/2015 |

OTHER PUBLICATIONS

V.G. Medina et al. "Elimination of Glycerol Production in Anaerobic Cultures of a *Saccharomyces cerevisiae* Strain Engineered To Use Acetic Acid as an Electron Acceptor", Applied ND Environmental Microbiology, vol. 76, No. 1 (Nov. 13, 2009), pp. 190-195.
International Search Report of PCT/EP2016/061099 dated Jul. 1, 2016.
Meaden, Philip G. et al., "The ALD6 Gene of *Saccharomyces cerevisiae* Encodes a Cytosolic, Mg2+—Activated Acetaldehyde Dehydrogenase" Yeast, 1997, pp. 1319-1327, vol. 13.
V.K. Jain. "Modifying redox potential and its impact on metabolic fluxes in *Saccharomyces cerevisiae*", Dissertation presented for the the degree of Doctor of Philosophy at Stellenbosch University Institute for Winebiotechnology, Faculty of AgriSciences (Year: 2010).
F. Remize et al. "Engineering of the Pyruvate Dehydrogenase Bypass in *Saccharomyces cerevisiae*: Role of the Cytosolic Mg2 and Mitochondrial K Acetaldehyde Dehydrogenases Ald6p and Ald4p in Acetate Formation during Alcoholic Fermentation", Applied and Environmental Microbiology, 66(8): 3151-3159 (Year: 2000).

* cited by examiner

*Primary Examiner* — Tekchand Saidha
(74) *Attorney, Agent, or Firm* — McBee Moore & Vanik IP, LLC

(57) ABSTRACT

The present invention relates to a yeast cell that is genetically modified comprising:
   a) a disruption of one or more aldehyde dehydrogenase (E.C:1.2.1.4) native to the yeast;
   b) one or more nucleotide sequence encoding a heterologous NAD+-dependent acetylating acetaldehyde dehydrogenase (E.C. 1.2.1.10);
   c) one or more nucleotide sequence encoding a homologous or heterologous acetyl-CoA synthetase (E.C. 6.2.1.1); and
   d) a modification that leads to reduction of glycerol 3-phosphate phosphohydrolase (E.C. 3.1.3.21) and/or glycerol 3-phosphate dehydrogenase (E.C. 1.1.1.8 or E.C. 1.1.5.3) activity, native to the yeast.

14 Claims, 7 Drawing Sheets

Specification includes a Sequence Listing.

SEQUENCE LISTING

```
<160> NUMBER OF SEQ ID NOS: 3

<210> SEQ ID NO 1
<211> LENGTH: 5005
<212> TYPE: DNA
<213> ORGANISM: Artificial Sequence
<220> FEATURE:
<223> OTHER INFORMATION: plasmid bearing loxP-kanMX-loxP sequence

<400> SEQUENCE: 1
gcttccggct cgtatgttgt gtggaattgt gagcggataa caatttcaca caggaaacag      60
ctatgaccat gattacgcca agctatttag gtgacactat agaatactca agctatgcat     120
caagcttggt accgagctcg gatccactag caatccttcg tataatgtat gctatacgaa     180
gttattctag taacggccgc cagtgtgctg gaattcgccc ttaagcttgc ctcgtcccg      240 ccgggtcacc cggccagcga catggaggcc cagaatacc tccttgacag tcttgacgtg      300
cgcagctcag gggcatgatg tgactgtcgc ccgtacattt agcccataca tccccatgta      360
taatcatttg catccataca ttttgatggc cgcacgcgc gaagcaaaaa ttacggctcc      420
tcgctgcaga cctgcgagca gggaaacgct cccctcacag acgcgttgaa ttgtccccac      480
gccgcgcccc tgtagagaaa tataaaaggt taggatttgc cactgaggtt cttctttcat      540
atacttcctt ttaaaatctt gctaggatac agttctcaca tcacatccga acataaacaa      600
ccatgggtaa ggaaaagact cacgtttcga ggccgcgatt aaattccaac atggatgctg      660
atttatatgg gtataaatgg gctcgcgata atgtcgggca atcaggtgcg acaatctatc      720
gattgtatgg gaagcccgat gcgccagagt tgtttctgaa acatggcaaa ggtagcgttg      780
ccaatgatgt tacagatgag atggtcagac taaactggct gacggaattt atgcctcttc      840
cgaccatcaa gcattttatc cgtactcctg atgatgcatg gttactcacc actgcgatcc      900
ccggcaaaac agcattccag gtattagaag aatatcctga ttcaggtgaa aatattgttg      960
atgcgctggc agtgttcctg cgccggttgc attcgattcc tgtttgtaat tgtccttta     1020 acagcgatcg cgtatttcgt ctcgctcagg cgcaatcacg aatgaataac ggtttggttg     1080
atgcgagtga ttttgatgac gagcgtaatg gctggcctgt tgaacaagtc tggaaagaaa     1140
tgcataagct tttgccattc tcaccggatt cagtcgtcac tcatggtgat ttctcacttg     1200
ataaccttat ttttgacgag gggaaattaa taggttgtat tgatgttgga cgagtcggaa     1260
tcgcagaccg ataccaggat cttgccatcc tatggaactg cctcggtgag ttttctcctt     1320
cattacagaa acggcttttt caaaaatatg gtattgataa tcctgatatg aataaattgc     1380
agtttcattt gatgctcgat gagttttct aatcagtact gacaataaaa agattcttgt     1440
tttcaagaac ttgtcatttg tatagtttt ttatattgta gttgttctat tttaatcaaa     1500
tgttagcgtg atttatattt tttttcgcct cgacatcatc tgcccagatg cgaagttaag     1560
tgcgcagaaa gtaatatcat gcgtcaatcg tatgtgaatg ctggtcgcta tactgctgtc     1620
```

-continued

```
gattcgatac taacgccgcc atccagtgtc gacgatatct agagcgcgca taacttcgta    1680
taatgtatgc tatacgaagt tataggatcc atcacactgg cggccgctcg agcatgcatc    1740
tagagggccc aattcgccct atagtgagtc gtattacaat tcactggccg tcgttttaca    1800
acgtcgtgac tgggaaaacc ctggcgttac ccaacttaat cgccttgcag cacatccccc    1860
tttcgccagc tggcgtaata gcgaagaggc ccgcaccgat cgcccttccc aacagttgcg    1920
cagcctatac gtacggcagt ttaaggttta cacctataaa agagagagcc gttatcgtct    1980
gtttgtggat gtacagagtg atattattga cacgccgggg cgacggatgg tgatccccct    2040
ggccagtgca cgtctgctgt cagataaagt ctcccgtgaa ctttacccgg tggtgcatat    2100
cggggatgaa agctggcgca tgatgaccac cgatatggcc agtgtgccgg tctccgttat    2160
cggggaagaa gtggctgatc tcagccaccg cgaaaatgac atcaaaaacg ccattaacct    2220
gatgttctgg ggaatataaa tgtcaggcat gagattatca aaaaggatct tcacctagat    2280
ccttttcacg tagaaagcca gtccgcagaa acggtgctga ccccggatga atgtcagcta    2340
ctgggctatc tggacaaggg aaaacgcaag cgcaaagaga agcaggtag  cttgcagtgg    2400
gcttacatgg cgatagctag actgggcggt tttatggaca gcaagcgaac cggaattgcc    2460
agctggggcg ccctctggta aggttgggaa gccctgcaaa gtaaactgga tggctttctc    2520
gccgccaagg atctgatggc gcaggggatc aagctctgat caagagacag gatgaggatc    2580
gtttcgcatg attgaacaag atggattgca cgcaggttct ccggccgctt gggtggagag    2640
gctattcggc tatgactggg cacaacagac aatcggctgc tctgatgccg ccgtgttccg    2700
gctgtcagcg caggggcgcc cggttctttt tgtcaagacc gacctgtccg gtgccctgaa    2760
tgaactgcaa gacgaggcag cgcggctatc gtggctggcc acgacgggcg ttccttgcgc    2820
agctgtgctc gacgttgtca ctgaagcggg aagggactgg ctgctattgg gcgaagtgcc    2880
ggggcaggat ctcctgtcat ctcaccttgc tcctgccgag aaagtatcca tcatggctga    2940
tgcaatgcgg cggctgcata cgcttgatcc ggctacctgc ccattcgacc accaagcgaa    3000
acatcgcatc gagcgagcac gtactcggat ggaagccggt cttgtcgatc aggatgatct    3060
ggacgaagag catcaggggc tcgcgccagc cgaactgttc gccaggctca aggcgagcat    3120
gcccgacggc gaggatctcg tcgtgaccca tggcgatgcc tgcttgccga atatcatggt    3180
ggaaaatggc cgcttttctg gattcatcga ctgtggccgg ctgggtgtgg cggaccgcta    3240
tcaggacata gcgttggcta cccgtgatat tgctgaagag cttggcggcg aatgggctga    3300
ccgcttcctc gtgctttacg gtatcgccgc tcccgattcg cagcgcatcg ccttctatcg    3360
ccttcttgac gagttcttct gaattattaa cgcttacaat ttcctgatgc ggtattttct    3420
ccttacgcat ctgtgcggta tttcacaccg catacaggtg cacttttcg gggaaatgtg    3480
cgcggaaccc ctatttgttt attttttctaa atacattcaa atatgtatcc gctcatgaga    3540
caataaccct gataaatgct tcaataatag cacgtgagga gggccaccat ggccaagttg    3600
accagtgccg ttccggtgct caccgcgcgc gacgtcgccg gagcggtcga ttctggacc    3660
gaccggctcg ggttctcccg ggacttcgtg gaggacgact tcgccggtgt ggtccgggac    3720
gacgtgaccc tgttcatcag cgcggtccag gaccaggtgg tgccggacaa caccctggcc    3780
tgggtgtggg tgcgcggcct ggacgagctg tacgccgagt ggtcggaggt cgtgtccacg    3840
aacttccggg acgcctccgg gccggccatg accgagatcg cgagcagcc  gtgggggcgg    3900
gagttcgccc tgcgcgaccc ggccggcaac tgcgtgcact cgtgccgga ggagcaggac    3960
tgacacgtgc taaaacttca ttttaatttt aaaaggatct aggtgaagat cctttttgat    4020
```

```
aatctcatga ccaaaatccc ttaacgtgag ttttcgttcc actgagcgtc agacccgta    4080 gaaaagatca aaggatcttc ttgagatcct ttttttctgc gcgtaatctg ctgcttgcaa   4140
acaaaaaaac caccgctacc agcggtggtt tgtttgccgg atcaagagct accaactctt   4200
tttccgaagg taactggctt cagcagagcg cagataccaa atactgtcct tctagtgtag   4260
ccgtagttag gccaccactt caagaactct gtagcaccgc ctacatacct cgctctgcta   4320
atcctgttac cagtggctgc tgccagtggc gataagtcgt gtcttaccgg gttggactca   4380
agacgatagt taccggataa ggcgcagcgg tcgggctgaa cggggggttc gtgcacacag   4440
cccagcttgg agcgaacgac ctacaccgaa ctgagatacc tacagcgtga gctatgagaa   4500
agcgccacgc ttcccgaagg gagaaaggcg gacaggtatc cggtaagcgg cagggtcgga   4560
acaggagagc gcacgaggga gcttccaggg ggaaacgcct ggtatcttta tagtcctgtc   4620
gggtttcgcc acctctgact tgagcgtcga ttttgtgat gctcgtcagg ggggcggagc    4680
ctatggaaaa acgccagcaa cgcggccttt ttacggttcc tgggcttttg ctggcctttt   4740
gctcacatgt tctttcctgc gttatcccct gattctgtgg ataaccgtat taccgccttt   4800
gagtgagctg ataccgctcg ccgcagccga acgaccgagc gcagcgagtc aagcgcccaa   4860
tacgcaaacc gcctctcccc gcgcgttggc cgattcatta atgcagctgg cacgacaggt   4920
ttcccgactg gaaagcgggc agtgagcgca acgcaattaa tgtgagttag ctcactcatt   4980
aggcacccca ggctttacac tttat                                          5005

<210> SEQ ID NO 2
<211> LENGTH: 70
<212> TYPE: DNA
<213> ORGANISM: Artificial Sequence
<220> FEATURE:
<223> OTHER INFORMATION: Primer 12388 (ald6 5flank forward)

<400> SEQUENCE: 2
gcagaaaaga ggggcagtgg cctgttttc gacataaatg aggggcatgg cgccaagcta    60
tttaggtgac                                                           70

<210> SEQ ID NO 3
<211> LENGTH: 70
<212> TYPE: DNA
<213> ORGANISM: Artificial Sequence
<220> FEATURE:
<223> OTHER INFORMATION: Primer 12389 (ald6 3flank reverse)

<400> SEQUENCE: 3
tccacgttag ttttctttgg atatagcagt tgttgtacac tagcttaaga tcactatagg    60
gcgaattggg                                                           70
```

ACETATE CONSUMING YEAST CELL

CROSS-REFERENCE TO RELATED APPLICATIONS

This application is a Continuation of U.S. application Ser. No. 15/575,538, filed 20 Nov. 2017, which is a National Stage entry of International Application No. PCT/EP2016/061099, filed 18 May 2016, which claims priority to European Patent Application No. 15168833.0, filed 22 May 2015. The content of each of these applications is herein incorporated by reference in their entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-465001_ST25.txt" created on 14 Jun. 2021, and 7,589 bytes in size) is submitted concurrently with the instant application, and the entire contents of the Sequence Listing are incorporated herein by reference.

BACKGROUND

Field of the Invention

The present invention relates to engineered microorganisms such as yeast. In particular the invention relates to acetic acid, pentose and glucose converting yeast cells with improved pentose conversion. The invention further relates to the processes wherein the yeast cells produce fermentation product such as ethanol.

Description of Related Art

Second generation bioethanol is produced from e.g. lignocellulosic fractions of plant biomass that is hydrolyzed into free monomeric sugars, such as hexoses and pentoses, for fermentation into ethanol. Apart from the sugar release during pretreatment and hydrolysis of the biomass, some toxic by-products are formed. For instance, furfural and HMF are two of these products. The quantities in which they are formed depend on several pretreatment parameters, such as temperature, pressure and pretreatment time. Lignocellulosic hydrolysates also contain high amounts of acetic acid, which is a potent inhibitor of the fermentative capacity of microorganisms, such as yeasts.

Glycerol is the major by-product during fermentation of sugars into ethanol, mainly formed as a result of re-oxidation reactions to consume the excess NADH formed during ethanol production under anaerobic conditions. As a result, during industrial fermentations, about 5 to 10% of the consumed sugars by yeast cells are diverted into glycerol. Lowering the amount of this polyol is considered a promising route to increase ethanol yield. This could be achieved by adjusting the feeding rate during the fed-batch process, or by selecting strains that produce less glycerol, however both approaches have relatively limited effect.

Several different approaches have been reported that could help to reduce the inhibitory effect of acetic acid on the fermenting capacity of the sugars in hydrolysates as well as (partly) solving redox balance issues upon deletion of the genes involved in glycerol production, e.g. by genetic engineering of yeasts.

Sonderegger et al (2004) discloses the heterologous expression of phosphotransacetylase and acetaldehyde dehydrogenase in a xylose-fermenting *Saccharomyces cerevisiae* strain. In combination with the native phosphoketolase, Sonderegger et al thereby created a functional phosphoketolase pathway that is capable of net reoxidation of NADH generated by the heterologous expression of a xylose reductase and xylitol dehydrogenase that are used for xylose utilization in that particular strain.

Guadalupe et al (2009) described a *Saccharomyces cerevisiae* strain wherein production of the by-product glycerol is eliminated by the disruption of the endogenous NAD-dependent glycerol 3-phosphate dehydrogenase genes (GPD1 and GPD2). Expression of the *E. coli* mhpF gene, encoding the acetylating NAD-dependent acetaldehyde dehydrogenase, restored the ability of the gpd1gpd2 double deletion strain to grow anaerobically by supplementation of the medium with acetic acid.

Yu et al (2010) constructed *Saccharomyces cerevisiae* strains metabolically engineered for improved ethanol production from glycerol by simultaneous overexpression of glycerol dehydrogenase (encoded by GCY1), dihydroxyacetone kinase (DAK1) and the glycerol uptake protein (GUP1). In a later report by the same group (Yu et al, 2011) it is described that additional overexpression of ADH1 and PDC1, encoding alcohol dehydrogenase and pyruvate decarboxylase respectively, caused an increase in growth rate and glycerol consumption under fermentative conditions, resulting in a slightly increased final ethanol yield.

Lee and Dasilva (2006) disclosed the yeast *Saccharomyces cerevisiae* engineered to produce 1,2-propanediol from glycerol by amongst others introducing expression of the *Escherichia coli* mgs and gldA genes.

The technology described by Guadelupe et al (and also in patent application WO 2011/010923) provides a solution for decreasing the acetic acid content of hydrolysates during fermentation of the biomass sugars and the aforementioned acetic acid into e.g. ethanol.

Further enhancement of the ability to convert acetic acid is potentially possible by introducing an extra NADH-generating pathway, e.g. by additionally (over-)expressing a glycerol consumption pathway. Upon introduction of the aforementioned GUP1-, GCY1- and DAK1-genes (Yu et al, 2010) in a yeast strain expressing an anaerobic acetic acid conversion pathway (such as e.g. described by Medina et al, 2009), acetic acid conversion should be increased in order to maintain the redox balance, leading to further increased detoxification of the hydrolysate and higher ethanol yield. The solution of Yu et al however, does not work, since the yeast glycerol dehydrogenase (encoded by GCY1) uses $NADP^+$ as a co-factor, resulting in a cofactor imbalance due to insufficient cofactor regeneration. An alternative glyceroldehydrogenase (gldA from *E. coli*) was tested in combination with the acetic acid reduction pathway and indeed enhanced the conversion of acetic acid under anaerobic growth (fermentation) conditions (patent application WO2013/081456). Nevertheless, there is still a need to improve the conversion of acetate, pentose and/or hexose to fermentation product.

SUMMARY OF THE INVENTION

It is therefore an object of the present invention to provide for yeasts that are capable of producing ethanol from acetic acid or acetate while retaining their abilities of fermenting hexoses (glucose, fructose, galactose, etc) as well as pentoses like xylose, as well as processes wherein these strains are used for the production of ethanol and/or other fermentation products.

Another object is to provide for cells, e.g. yeast cells that are capable of producing ethanol from glycerol and/or glycerol and acetic acid while retaining their abilities of fermenting hexoses (glucose, fructose, galactose, etc) as well as pentoses like xylose. Another object is to increase the production of fermentation product (yield, production rate or both). In an embodiment thereof the yeast produces less glycerol.

Further, it is an object of the invention to provide a yeast strain that can an-aerobically co-ferment acetate, pentose and glucose.

It is an object of the present invention to provide a cost-effective method of producing ethanol by fermentation of pentose and/or acetate.

It is another object of the present invention to provide a yeast cell that is capable of fermenting pentose at a higher rate than can be achieved using strains currently known to the art.

It is another object to reduce the fermentation time of C5/C6 fermentation.

Other objects, features, and advantages of the invention will be apparent from review of the specification and claims.

One or more of these objects are attained according to the invention that provides a yeast cell that is genetically modified comprising:

a) a disruption of one or more aldehyde dehydrogenase native to the yeast;

b) one or more nucleotide sequence encoding a heterologous NAD+-dependent acetylating acetaldehyde dehydrogenase (E.C. 1.2.1.10);

c) one or more nucleotide sequence encoding a homologous or heterologous acetyl-CoA synthetase (E.C. 6.2.1.1); and d) a modification that leads to reduction of glycerol 3-phosphate phosphohydrolase and/or glycerol 3-phosphate dehydrogenase activity, compared to the yeast without such modification.

In an embodiment the one or more aldehyde dehydrogenase (E.C:1.2.1.4) native to the yeast in d) is a acetaldehyde dehydrogenase-6 (ALD6) native to the yeast.

The invention further relates to a process for preparation of a pentose fermenting yeast cell, wherein a yeast cell comprising one or more exogenous genes of a pentose pathway is subjected to disruption of the gene ALD6 native to the yeast cell.

The invention further relates to fermentation process wherein lignocellulosic sugar is converted by the disruptant yeast cell to fermentation product. In an embodiment thereof the fermentation product is ethanol.

The invention further relates to a process of aerobic propagation of an acetate consuming yeast.

DETAILED DESCRIPTION OF A PREFERRED EMBODIMENT

Brief Description of the Sequence Listing

Figure 1:
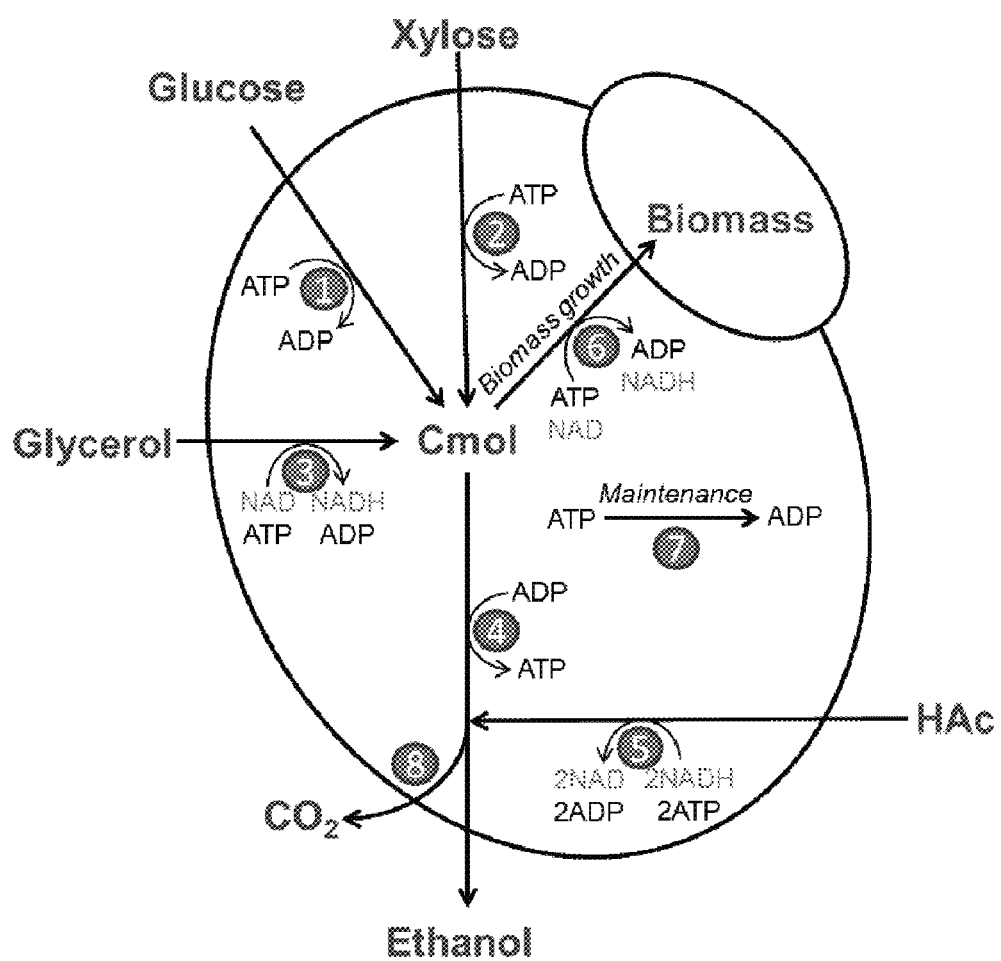
FIG. 1 shows a scheme of mathematical model (minimal—model approach). The numbers indicate the following processes: 1.) glucose uptake and metabolism (upper-glycolysis), 2.) xylose uptake and metabolism, 3.) glycerol uptake and metabolism, 4.) ethanol formation (lower glycolysis), 5.) acetate uptake and metabolism, 6.) biomass formation, 7.) ATP turnover for maintenance, 8.) CO2 and ethanol production.

SEQ ID NO: 1 pRN772 (plasmid bearing loxP-kanMX-loxP sequence)

SEQ ID NO: 2 Primer 12388 (ald6 5'flank forward)

SEQ ID NO: 3 Primer 12389 (ald6 3'flank reverse)

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element. By way of example, cell can herein be one cell, but refer also to a population of cells or a strain.

"Yeast" is herein defined as eukaryotic microorganism and include all species of the subdivision Eumycotina that predominantly grow in unicellular form. Yeasts may either grow by budding of a unicellular thallus or may grow by fission of the organism. Preferred yeasts cells for use in the present invention belong to the genera *Saccharomyces, Kluyveromyces, Candida, Pichia, Schizosaccharomyces, Hansenula, Kloeckera, Schwanniomyces,* and *Yarrowia*. In an embodiment thereof the yeast cell belongs to a species selected from the group consisting of *S. cerevisiae, S. exiguus, S. bayanus, K. lactis, K. marxianus* and *Schizosaccharomyces pombe*. In an embodiment the yeast cell is of the species *Saccharomyces cerevisiae*. Preferably the yeast is capable of anaerobic fermentation, more preferably anaerobic alcoholic fermentation.

"Disruption" is herein understood to mean any disruption of activity, and includes, but is not limited to deletion, mutation, reduction of the affinity of the disrupted gene and expression of antisense RNA complementary to ALD6 mRNA. A gene disruptant is a cell that has one or more disruption of the respective gene. Native to yeast herein is understood as that the gene is present in the yeast cell before the disruption. It includes the situation that the gene native to yeast is present in a wild-type yeast cell, a laboratory yeast cell or an industrial yeast cell. Yeast cell may herein also be designated as yeast strain or as part of yeast strain.

The various embodiments of the invention described herein may be cross-combined.

The invention provides a yeast cell that is genetically modified comprising:
a) a disruption of one or more aldehyde dehydrogenase (E.C:1.2.1.4) native to the yeast;
b) one or more nucleotide sequence encoding a heterologous NAD+-dependent acetylating acetaldehyde dehydrogenase (E.C. 1.2.1.10);
c) one or more nucleotide sequence encoding a homologous or heterologous acetyl-CoA synthetase (E.C. 6.2.1.1); and
d) a modification that leads to reduction of glycerol 3-phosphate phosphohydrolase and/or glycerol 3-phosphate dehydrogenase activity, compared to the disruptant yeast without such modification.

In an embodiment of the invention, the one or more aldehyde dehydrogenase (E.C:1.2.1.4) native to the yeast in c) is a acetaldehyde dehydrogenase-6 (ALD6).

A cell with one or more disruption(s) of aldehyde dehydrogenase is herein designated as disruptant yeast cell. The cell with disruption of the ALD6 gene is herein also called disruptant yeast cell.

In an embodiment, the yeast cell comprises further:
e) one or more nucleotide sequence encoding a heterologous xylose isomerase (E.C. 5.3.1.5);
f) one or more nucleotide sequence encoding a heterologous glycerol dehydrogenase (E.C. 1.1.1.6); and
g) one or more nucleotide sequence encoding a homologous or heterologous dihydroxyacetone kinase (E.C. 2.7.1.28 or E.C. 2.7.1.29).

The disruptant yeast cell may be haploid, diploid or polyploid. In diploid or polyploid strains, in one embodiment, the features a) to g) may be individually or in any combination present in in one allele of the diploid or polyploid strain. In another embodiment they may be in all alleles. For polyploid strains the features a) to g) individually or in any combination may be present in a majority of the alleles or alternatively in a minority of the alleles.

These features and other embodiments of the invention are hereafter described in more detail.

a) A Disruption of One or More Aldehyde Dehydrogenase (E.C. 1.2.1.4) Native to the Yeast The enzyme that is disrupted according to the invention is an aldehyde dehydrogenase aldehyde dehydrogenase (E.C: 1.2.1.4) native to the yeast.

In an embodiment the aldehyde dehydrogenase native to the yeast is acetaldehyde dehydrogenase-6 (ALD6).

ALD6 is herein any Mg2+ activated enzyme that catalyses the dehydrogenation of acetaldehyde into acetate, and vice-versa.

The ALD6 reaction is:

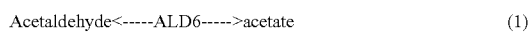

Acetaldehyde<-----ALD6----->acetate (1)

Figure 4:
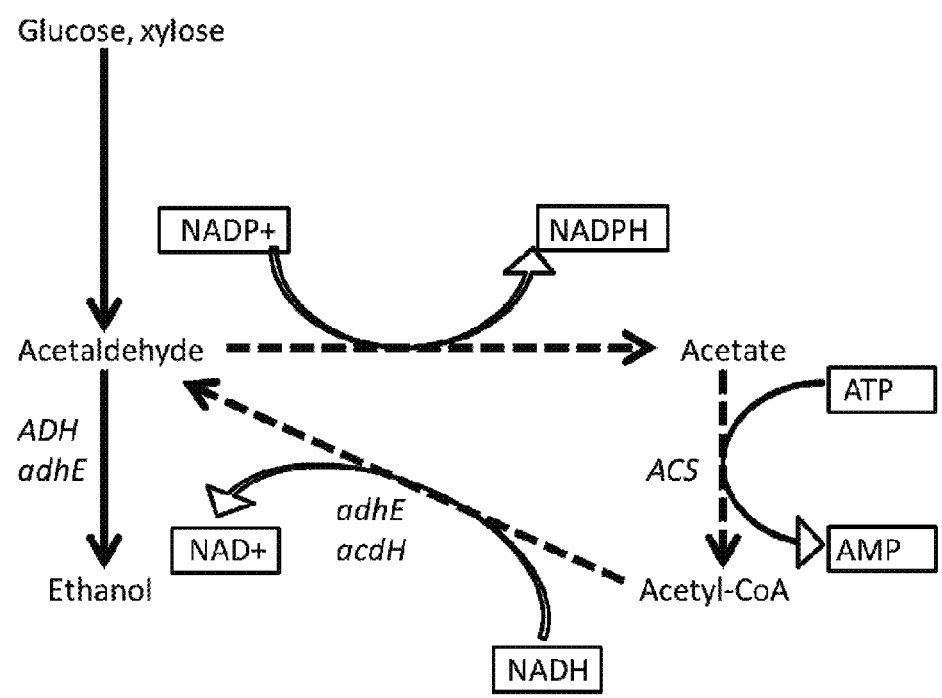
FIG. 4 shows a schematic overview of the metabolic pathways involved in futile cycling of acetaldehyde—acetate—acetyl-CoA, causing an increased maintenance ATP. The futile cycle is indicated by dotted arrows. The acetylating acetaldehyde dehydrogenase (adhE, acdH) was introduced in the strain to enable acetate to ethanol conversion.

Without being limiting for the scope of the invention, the following explanation in retrospect may be given. As shown in the examples, a mathematical model confirmed that decreasing the maintenance ATP demand will increase the sugar to ethanol conversion rates (see, Example 1). A possible source of maintenance ATP turnover is futile cycling. To enable acetate to ethanol conversion an acetylating acetaldehyde dehydrogenase (e.g., adhE or acdH) was introduced in the strains (see WO2015028583 and WO2015028582). This also introduced a possible futile cycle in the strains, see FIG. 4.

FIG. 1 shows a schematic overview of the metabolic pathways involved in futile cycling of acetaldehyde—acetate—acetyl-CoA, causing an increased maintenance ATP. The futile cycle is indicated by dotted arrows. The acetylating acetaldehyde dehydrogenase (adhE, acdH) was introduced in the strain to enable acetate to ethanol conversion.

Disruption of the futile cycle led to decrease the maintenance ATP and thereby improve the glucose and xylose to ethanol conversion in Example 1. The target for disruption of the futile cycle is the enzyme catalyzing the acetaldehyde to acetate conversion in the cytoplasm (ALD6). The ACS or acetylating acetaldehyde dehydrogenase cannot be a target for disrupting the futile cycle because these enzymes are part of the acetate to ethanol conversion pathway.

In an embodiment of the invention, the yeast cell is a strain wherein reduced expression of ALD6 in the yeast variant is effected by a means selected from the group consisting of disruption of the ALD6 gene and expression of antisense RNA complementary to ALD6 mRNA.

In an embodiment of the invention the yeast cell is an ALD6 disruptant of *Saccharomyces cerevisiae*.

In another embodiment the yeast cell is *Saccharomyces cerevisiae* YD01247ΔALD6 or YD01248ΔALD6. Suitable ALD6 nucleotide sequences for disruption with identity to the ALD6 nucleotide sequence of *Saccharomyces cerevisiae* in other yeasts are given in table 1.

TABLE 1

Suitable ALD6 nucleotide sequences for disruption occurring in different types of yeast

| Sequence and Organism | Accession number | % ID |
| --- | --- | --- |
| aldehyde dehydrogenase (NADP(+)) ALD6 [*Saccharomyces cerevisiae* S288c] | NP_015264.1 | 100 |
| Ald6p [*Saccharomyces cerevisiae* AWRI796] | EGA72659.1 | 99 |
| Aldehyde dehydrogenase 6 [*Saccharomyces cerevisiae* × *Saccharomyces kudriavzevii*] | CCD31406.1 | 97 |
| hypothetical protein NDAI_0E02900 [*Naumovozyma dairenensis* CBS 421] | XP_003670350.1 | 80 |
| magnesium-activated aldehyde dehydrogenase [*Kluyveromyces marxianus* DMKU3-1042] | BAP69922.1 | 74 |
| aldehyde dehydrogenase (NAD+) [*Wickerhamomyces ciferrii*] | XP_011273253.1 | 63 |
| aldehyde dehydrogenase [*Brettanomyces bruxellensis* AWRI1499] [*Dekkera bruxellensis* AWRI1499] | EIF46557.1 | 56 | b) Acetaldehyde Dehydrogenase (Acetylating) (EC 1.2.1.10).

The cell of the invention further comprises an exogenous gene coding for an enzyme with the ability to reduce acetylCoA into acetaldehyde, which gene confers to the cell the ability to convert acetylCoA (and/or acetic acid) into ethanol. An enzyme with the ability to reduce acetylCoA into acetaldehyde is herein understood as an enzyme which catalyzes the reaction (ACDH; EC 1.2.1.10):

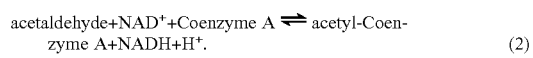

acetaldehyde+NAD$^+$+Coenzyme A ⇌ acetyl-Coenzyme A+NADH+H$^+$. (2)

Thus, the enzyme catalyzes the conversion of acetylCoA into acetaldehyde (and vice versa) and is also referred to as an (acetylating NAD-dependent) acetaldehyde dehydrogenase or an acetyl-CoA reductase. The enzyme may be a bifunctional enzyme which further catalyzes the conversion of acetaldehyde into ethanol (and vice versa; see below). For convenience we shall refer herein to an enzyme having at least the ability to reduce acetylCoA into either acetaldehyde or ethanol as an "acetaldehyde dehydrogenase". It is further understood herein that the cell has endogenous alcohol dehydrogenase activities which allow the cell, being provided with acetaldehyde dehydrogenase activity, to complete the conversion of acetyl-CoA into ethanol. Further the cell has endogenous or exogenous acetyl-CoA synthetase, which allows the cell, being provided with acetaldehyde dehydrogenase activity, to complete the conversion of acetic acid (via acetyl-CoA) into ethanol.

The exogenous gene may encode for a monofunctional enzyme having only acetaldehyde dehydrogenase activity (i.e. an enzyme only having the ability to reduce acetylCoA into acetaldehyde) such as e.g. the acetaldehyde dehydrogenase encoded by the *E. coli* mhpF gene. Suitable examples of prokaryotes comprising monofunctional enzymes with acetaldehyde dehydrogenase activity are provided in Table 2. The amino acid sequences of these monofunctional enzymes are available in public databases and can be used by the skilled person to design codon-optimized nucleotide sequences coding for the corresponding monofunctional enzyme.

TABLE 2

Suitable enzymes with acetaldehyde dehydrogenase activity and identity to *E. coli* mhpF

| Sequence and Organism | Amino acid identity (%) |
|---|---|
| *Escherichia coli* str. K12 substr. MG1655 | 100% |
| *Shigella sonnei* | 100% |
| *Escherichia coli* IAI39 | 99% |
| *Citrobacter youngae* ATCC 29220 | 93% |
| *Citrobacter* sp. 30_2 | 92% |
| *Klebsiella pneumoniae* 342) | 87% |
| *Klebsiella variicola* | 87% |
| *Pseudomonas putida* | 81% |
| *Ralstonia eutropha* JMP134 | 82% |
| *Burkholderia* sp. H160 | 81% |
| *Azotobacter vinelandii* DJ | 79% |
| *Ralstonia metallidurans* CH34 | 70% |
| *Xanthobacter autotrophicus* Py2 | 67% |
| *Burkholderia cenocepacia* J2315 | 68% |
| *Frankia* sp. EAN1pec | 67% |
| *Polaromonas* sp. JS666 | 68% |
| *Burkholderia phytofirmans* PsJN | 70% |
| *Rhodococcus opacus* B4 | 64% |

In an embodiment, the cell comprises an exogenous gene coding for a bifunctional enzyme with acetaldehyde dehydrogenase and alcohol dehydrogenase activity, which gene confers to the cell the ability to convert acetylCoA into ethanol. The advantage of using a bifunctional enzyme with acetaldehyde dehydrogenase and alcohol dehydrogenase activities as opposed to separate enzymes for each of the acetaldehyde dehydrogenase and alcohol dehydrogenase activities, is that it allows for direct channeling of the intermediate between enzymes that catalyze consecutive reactions in a pathway offers the possibility of an efficient, exclusive, and protected means of metabolite delivery. Substrate channeling thus decreases transit time of intermediates, prevents loss of intermediates by diffusion, protects labile intermediates from solvent, and forestalls entrance of intermediates into competing metabolic pathways. The bifunctional enzyme therefore allows for a more efficient conversion of acetylCoA into ethanol as compared to the separate acetaldehyde dehydrogenase and alcohol dehydrogenase enzymes. A further advantage of using the bifunctional enzyme is that it may also be used in cells having little or no alcohol dehydrogenase activity under the condition used, such as e.g. anaerobic conditions and/or conditions of catabolite repression.

Bifunctional enzymes with acetaldehyde dehydrogenase and alcohol dehydrogenase activity are known in the art prokaryotes and protozoans, including e.g. the bifunctional enzymes encoded by the *Escherichia coli* adhE and *Entamoeba histolytica* ADH2 genes (see e.g. Bruchaus and Tannich, 1994, J. Biochem. 303: 743-748; Burdette and Zeikus, 1994, J. Biochem. 302: 163-170; Koo et al., 2005, Biotechnol. Lett. 27: 505-510; Yong et al., 1996, Proc Natl Acad Sci USA, 93: 6464-6469). Bifunctional enzymes with acetaldehyde dehydrogenase and alcohol dehydrogenase activity are larger proteins consisting of around 900 amino acids and they are bifunctional in that they exhibit both acetaldehyde dehydrogenase (ACDH; EC 1.2.1.10) and alcohol dehydrogenase activity (ADH; EC 1.1.1.1). The *E. coli* adhE and *Entamoeba histolytica* ADH2 show 45% amino acid identity.

TABLE 3

Suitable bifunctional enzymes with acetaldehyde dehydrogenase and alcohol dehydrogenase activity and identity to *E. coli* adhE

| Sequence and Organism | Amino acid identity (%) |
|---|---|
| *Escherichia coli* O157:H7 str. Sakai | 100% |
| *Shigella sonnei* | 100% |
| *Shigella dysenteriae* 1012 | 99% |
| *Klebsiella pneumoniae* 342 | 97% |
| *Enterobacter* sp. 638 | 94% |
| *Yersinia pestis* biovar Microtus str. 91001 | 90% |
| *Serratia proteamaculans* 568 | 90% |
| *Pectobacterium carotovorum* WPP14 | 90% |
| *Sodalis glossinidius* str. 'morsitans' | 87% |
| *Erwinia tasmaniensis* Et1/99 | 86% |
| *Aeromonas hydrophila* ATCC 7966 | 81% |
| *Vibrio vulnificus* YJ016] | 76% |

TABLE 4

Suitable bifunctional enzymes with acetaldehyde dehydrogenase and alcohol dehydrogenase activity and identity to *Entamoeba histolytica* ADH2

| Sequence and Organism | Amino acid identity (%) |
|---|---|
| *Entamoeba histolytica* HM-1:IMSS | 99% |
| *Entamoeba dispar* SAW760 | 98% |
| *Mollicutes bacterium* D7 | 65% |
| *Fusobacterium mortiferum* ATCC 9817 | 64% |
| *Actinobacillus succinogenes* 130Z | 63% |
| *Pasteurella multocida* Pm70 | 62% |
| *Mannheimia succiniciproducens* MBEL55E | 61% |
| *Streptococcus* sp. 2_1_36FAA] | 61% |

For expression of the nucleotide sequence encoding the bifunctional enzyme having acetaldehyde dehydrogenase and alcohol dehydrogenase activities, or the enzyme having acetaldehyde dehydrogenase activity, the nucleotide sequence (to be expressed) is placed in an expression construct wherein it is operably linked to suitable expression regulatory regions/sequences to ensure expression of the enzyme upon transformation of the expression construct into the cell of the invention (see above). Suitable promoters for expression of the nucleotide sequence coding for the enzyme having the bifunctional enzyme having acetaldehyde dehydrogenase and alcohol dehydrogenase activities, or the enzyme having acetaldehyde dehydrogenase activity include promoters that are preferably insensitive to catabolite (glucose) repression, that are active under anaerobic conditions and/or that preferably do not require xylose or arabinose for induction. Examples of such promoters are given above.

Preferably, the nucleotide sequence encoding the bifunctional enzyme having acetaldehyde dehydrogenase and alcohol dehydrogenase activities, or the enzyme having acetaldehyde dehydrogenase activity is adapted to optimize its codon usage to that of the cell in question (as described above).

c) Acetyl-CoA Synthetase (EC 6.2.1.1):

The cell of the invention comprises a gene coding for an enzyme that has the specific activity of Acetyl-CoA synthetase. Acetyl-CoA synthetase or Acetate-CoA ligase is an enzyme (EC 6.2.1.1) involved in metabolism of carbon sugars. It is in the ligase class of enzymes, meaning that it catalyzes the formation of a new chemical bond between two large molecules.

The two molecules joined by acetyl-CoA synthetase are acetate and coenzyme A (CoA). The complete reaction with all the substrates and products included is:

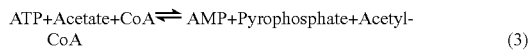

(3)

The Acs1 form of acetyl-CoA synthetase is encoded by the gene ACS1, which is activated by acetate and deactivated by glucose. The Acs2 form of acetyl-CoA synthetase is encoded by the gene ACS2, which is activated by acetate and deactivated by glucose.

Suitable examples of enzymes with acetyl-CoA synthetase activity are provided in Table 5.

TABLE 5

Suitable ACS's with identity to
Acs2 protein of *Saccharomyces cerevisiae*.

| Sequnce and organism | Identity (%) | Accession number |
|---|---|---|
| acetate--CoA ligase ACS2 [*Saccharomyces cerevisiae* S288c] | 100 | NP_013254.1 |
| acetyl CoA synthetase [*Saccharomyces cerevisiae* YJM789] | 99 | EDN59693.1 |
| acetate--CoA ligase [*Kluyveromyces lactis* NRRL Y-1140] | 85 | XP_453827.1 |
| acetate--CoA ligase [*Candida glabrata* CBS 138] | 83 | XP_445089.1 |
| acetate--CoA ligase [*Scheffersomyces stipitis* CBS 6054] | 68 | XP_001385819.1 |
| acetyl-coenzyme A synthetase FacA [*Aspergillus fumigatus* A1163] | 63 | EDP50475.1 |
| acetate--CoA ligase facA-Penicillium chrysogenum [*Penicillium chrysogenum* Wisconsin 54-1255] | 62 | XP_002564696.1 | d) A Modification that Leads to Reduction of Glycerol 3-Phosphate Phosphohydrolase and/or Glycerol 3-Phosphate Dehydrogenase Activity The disruptant yeast cell further may further comprise a modification that leads to reduction of glycerol 3-phosphate phosphohydrolase and/or glycerol 3-phosphate dehydrogenase activity, compared to the disruptant yeast without such modification.

In that embodiment, the cell may comprises a disruption of one or more endogenous nucleotide sequence encoding a glycerol 3-phosphate phosphohydrolase and/or encoding a glycerol 3-phosphate dehydrogenase gene.

In such embodiment the enzymatic activity needed for the NADH-dependent glycerol synthesis is reduced or deleted. The reduction or deleted of this enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encodes a polypeptide with reduced activity.

Such modifications can be carried out using commonly known biotechnological techniques, and may in particular include one or more knock-out mutations or site-directed mutagenesis of promoter regions or coding regions of the structural genes encoding GPD and/or GPP.

Alternatively, yeast strains that are defective in glycerol production may be obtained by random mutagenesis followed by selection of strains with reduced or absent activity of GPD and/or GPP. *S. cerevisiae* GPD1, GPD2, GPP1 and GPP2 genes are shown in WO2011010923, and are disclosed in SEQ ID NO: 24-27 of that application.

Thus, in the cells of the invention, the specific glycerol 3-phosphate phosphohydrolase and/or encoding a glycerol 3-phosphate dehydrogenase gene may be reduced. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the reduction in specific activity, preferably under anaerobic conditions. Glycerolphosphate dehydrogenase activity may be determined as described by Overkamp et al. (2002, Yeast 19:509-520).

A preferred gene encoding a glycerolphosphate dehydrogenase whose activity is to be reduced or inactivated in the cell of the invention is the *S. cerevisiae* GPD1 as described by van den Berg and Steensma (1997, Yeast 13:551-559), encoding the amino acid sequence GPD1 and orthologues thereof in other species.

Suitable examples of organisms (hosts) comprising an enzyme with glycerolphosphate dehydrogenase activity belonging to the genus *Saccharomyces, Naumovozyna, Candida Vanderwaltozyma* and *Zygosaccharomyces* are provided in Table 6.

TABLE 6

| Enzymes with glycerolphosphate dehydrogenase (GPD1) activity | |
|---|---|
| Sequence and Organism | Amino acid identity (%) |
| *S. cerevisiae* | 100% |
| *Naumovozyma dairenensis* | 79% |
| *Naumovozyma castellii* | 80% |
| *Candida glabrata* | 77% |
| *Vanderwaltozyma polyspora* | 77% |
| *Zygosaccharomyces rouxii* | 74% |
| *Saccharomycesis fibuligera* | 61% |

However, in some strains e.g. of *Saccharomyces, Candida* and *Zygosaccharomyces* a second gene encoding a glycerolphosphate dehydrogenase is active, i.e. the GPD2, see e.g. Overkamp et al. (2002, supra). Another preferred gene encoding a glycerolphosphate dehydrogenase whose activity is to be reduced or inactivated in the cell of the invention therefore is an *S. cerevisiae* GPD2 as described by Overkamp et al. (2002, supra), encoding the amino acid sequence GPD2 and orthologues thereof in other species.

Suitable examples of organisms (hosts) comprising an enzyme with glycerolphosphate dehydrogenase activity belonging to the genus (Zygo) *Saccharomyces* and *Candida* are provided in Table 7.

TABLE 7

Enzymes with glycerol phosphate
dehydrogenase (GPD2) activity

| Sequence and Organism | Amino acid identity (%) |
|---|---|
| *S. cerevisiae* | 100% |
| *Candida glabrata* | 75% |
| *Zygosaccharomyces rouxii* | 73% |
| *Spathaspora passalidarum* | 62% |
| *Scheffersomyces stipitis* | 61% |

In an embodiment, the cell is a yeast wherein the genome of the yeast cell comprises a disruption in at least one gene selected from the group of GPD1, GPD2, GPP1 and GPP2.

e) Xylose Isomerase (E.C. 5.3.1.5)

In an embodiment, the disruptant yeast cell comprises a xylose isomerase ((E.C. 5.3.1.5); xylA).

A "xylose isomerase" (E.C. 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). Generally a xylose isomerase requires a bivalent cation, such as magnesium, manganese or cobalt as a cofactor.

f) Glycerol Dehydrogenase (EC 1.1.1.6)

A glycerol dehydrogenase is herein understood as an enzyme that catalyzes the chemical reaction (EC 1.1.1.6):

$$glycerol + NAD^+ \rightleftharpoons glycerone + NADH + H^+ \quad (4)$$

Other names in common use include glycerin dehydrogenase, NAD-linked glycerol dehydrogenase and glycerol: NAD+2-oxidoreductase. Preferably the genetic modification causes overexpression of a glycerol dehydrogenase, e.g. by overexpression of a nucleotide sequence encoding a glycerol dehydrogenase. The nucleotide sequence encoding the glycerol dehydrogenase may be endogenous to the cell or may be a glycerol dehydrogenase that is heterologous to the cell. Nucleotide sequences that may be disrupted in the cells of the invention are e.g. the glycerol dehydrogenase gene from *S. cerevisiae* (GCY1) as e.g. described by Oechsner et al. (1988, FEBS Lett. 238: 123-128) or Voss et al. (1997, Yeast 13: 655-672).

g) One or More Nucleotide Sequence Encoding a Homologous or Heterologous Dihydroxyacetone Kinase (E.C. 2.7.1.28 or E.C. 2.7.1.29)

A dihydroxyacetone kinase is herein understood as an enzyme that catalyzes one of the chemical reactions:
EC 2.7.1.28 ATP+D-glyceraldehyde<=>ADP+D-glyceraldehyde 3-phosphate

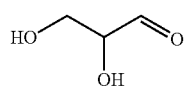

EC 2.7.1.29 ATP+glycerone[1]<=>ADP+glycerone phosphate

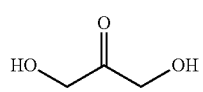

[1]glycerone=dihydroxyacetone.

Other names in common use include glycerone kinase, ATP:glycerone phosphotransferase and (phosphorylating) acetol kinase. It is understood that glycerone and dihydroxyacetone are the same molecule. Preferably the genetic modification causes overexpression of a dihydroxyacetone kinase, e.g. by overexpression of a nucleotide sequence encoding a dihydroxyacetone kinase. The nucleotide sequence encoding the dihydroxyacetone kinase may be endogenous to the cell or may be a dihydroxyacetone kinase that is heterologous to the cell. Nucleotide sequences that may be used for overexpression of dihydroxyacetone kinase in the cells of the invention are e.g. the dihydroxyacetone kinase genes from *S. cerevisiae* (DAK1) and (DAK2) as e.g. described by Molin et al. (2003, J. Biol. Chem. 278:1415-1423).

Suitable examples of enzymes with glycerol dehydrogenase activity are provided in Table 8.

TABLE 8

Suitable GCY's with identity to Gcy1
protein of *Saccharomyces cerevisiae* GCY1.

| Sequence and Organism | Identity (%) | Accession number |
|---|---|---|
| Gcy1p | 100% | NP_014763.1 |
| [*Saccharomyces cerevisiae* S288c] | | |
| GCY1-like protein | 89% | EJT43197.1 |
| [*Saccharomyces kudriavzevii* IFO 1802] | | |
| hypothetical protein KNAG_0C04910 | 69% | CCK69592.1 |
| [*Kazachstania naganishii* CBS 8797] | | |
| Ypr1p | 65% | NP_010656.1 |
| [*Saccharomyces cerevisiae* S288c] | | |
| Aldo/keto reductase | 55% | XP_001383482.1 |
| [*Scheffersomyces stipitis* CBS 6054] | | |
| >gb|ABN65453.1 | | |

Suitable examples of enzymes with dihydroxy acetone kinase activity are provided in Table 9.

TABLE 9

Suitable DAK's with identity to
Dak1 protein of *Saccharomyces cerevisiae*.

| Sequence and Organism | Identity (%) | Accession No. |
|---|---|---|
| Dak1p | 100 | NP_013641.1 |
| [*Saccharomyces cerevisiae* S288c] | | |
| dihydroxyacetone kinase | 99 | EDN64325.1 |
| [*Saccharomyces cerevisiae* YJM789] | | |
| DAK1-like protein | 95 | EJT44075.1 |
| [*Saccharomyces kudriavzevii* IFO 1802] | | |
| ZYBA0S11-03576g1_1 | 77 | CDF91470.1 |
| [*Zygosaccharomyces bailii* CLIB 213] | | |
| hypothetical protein | 70 | XP_451751.1 |
| [*Kluyveromyces lactis* NRRL Y-1140] | | |
| hypothetical protein | 63 | XP_449263.1 |
| [*Candida glabrata* CBS 138] | | |
| Dak2p | 44 | NP_116602.1 |
| [*Saccharomyces cerevisiae* S288c] | | |

The embodiments of the invention are now described in more detail.

In an embodiment the yeast cell has a overall ethanol production rate that is at least about 20% higher, at least about 50% or at least about 100% higher than that of the corresponding wild-type yeast.

The invention further relates to the use of a disruption of one or more ALD6 in yeast that leads to elimination of a futile ATP consuming cycle in the yeast.

The present invention is a yeast cell that ferments pentose in sugar mixtures that also contain glucose at a higher rate than the corresponding wild-type yeast, the yeast cell characterized by reduced expression of ALD6.

The present invention is also a method of producing ethanol from the fermentation of pentose, comprising the step of: culturing a yeast cell in a pentose-containing material under suitable fermentation conditions for a period of time sufficient to allow the fermentation of pentose to ethanol, the yeast variant being capable of fermenting pentose at a high rate relative to the corresponding wild-type yeast and having reduced expression of ALD6.

In another alternative embodiment of disruptant yeast, the promotor region for the functional ALD6 is replaced by a promoter that responds to diminished oxygen by down-regulating expression of the ALD6 gene.

In an alternative embodiment of the disruptant yeast, expression of ALD6 may be down-regulated through the use of an antisense construct in which part or all of the antisense strand coding for ALD6 is expressed under the regulation of a promotor that responds to diminished oxygen. In this embodiment, the antisense mRNA for ALD6 is expressed under oxygen limiting conditions and thereby inactivates the functional ALD6.

The yeast cell of the present invention is a ALD6 disruptant. By a ALD6 disruptant, it is meant a variant in which a part or all of the native gene is removed or replaced with DNA of which the expression does not result in a expression product having any function of the native ALD6.

By "wild-type" yeast, it is meant a pentose-fermenting yeast strain with normal levels of functional ALD6 from which the yeast cell of the present invention is derived. In certain cases, the "wild-type yeast" as defined in this patent application, may include mutagenized yeast. For example, the *Saccharomyces cerevisiae* strain YD01247 and YD01248, is itself a mutated yeast strain. However, YD01247 or YD01248 is also wild-type yeast, as defined herein, because it is a pentose-fermenting yeast with normal levels of functional ALD6 that was used to develop a yeast cell of the present invention.

According to the examples disruption of native ALD6 activity leads to shorter fermentation time in C5/C6 fermentation and/or to co-consumption by the yeast cell of pentose and glucose.

The resultant yeast cells, in the examples, designated as YD1247ΔALD6 and YD1248ΔALD6 were obtained and has been characterized as described in detail below in the examples. It is anticipated that a yeast cell of *S. cerevisiae* characterized by reduced expression of functional ALD6 gene and increased overall ethanol yield may be obtained by means other than eliminating the ALD6 gene by one step site-specific integration using a disruption cassette. For example, a variant lacking functional ALD6, or which expresses ALD6 at a reduced level, could be obtained by any of several means known to the art, such as exposing yeast cells to DNA-intercalating agents or irradiating yeast cells with ultra violet light. It is likely that ALD6 deficient cells could be distinguished from wild type cells on the basis of colony size and other morphological patterns (i.e., petite size, yellow colonies with a wrinkled appearance). The ALD6 status of putative ALD6 deficient colonies presumptively identified on the basis of this unique phenotype could be confirmed by for instance by ALD6 activity determinations.

The disruptant yeast cell typically contains genes of a pentose metabolic pathway non-native to the yeast and/or that allow the yeast cell to convert pentose(s). In one embodiment, the yeast cell may comprise one or two or more copies of one or more xylose isomerases and/or one or two or more copies of one or more xylose reductase and xylitol dehydrogenase genes, allowing the yeast cell to convert xylose. In an embodiment thereof, these genes may be integrated into the yeast cell genome. In another embodiment, the yeast cell comprises the genes araA, araB and araD. It is then able to ferment arabinose. In one embodiment of the invention the yeast cell comprises xylA-gene, XYL1 gene and XYL2 gene and/or XKS1-gene, to allow the yeast cell to ferment xylose; deletion of the aldose reductase (GRE3) gene; overexpression of PPP-genes, TAL1, TKL1, RPE1 and RKI1 to allow the increase of the flux through the pentose phosphate path-way in the cell, and/or overexpression of GAL2 and/or deletion of GAL80. Thus though inclusion of the above genes, suitable pentose or other metabolic pathway(s) may be introduced in the yeast cell that were non-native to the (wild type) yeast cell. According to an embodiment, the following genes may be introduced in the disruptant yeast cell by introduction into a host cell:

1) a cluster consisting of PPP-genes TAL1, TKL1, RPE1 and RKI1, optionally under control of strong constitutive promoter;
2) a cluster consisting of a xylA-gene under control of strong constitutive promoter;
3) a cluster comprising a XKS1-gene under control of strong constitutive promoter, 4) a cluster consisting of the genes araA, araB and araD under control of a strong constitutive promoter
5) deletion of an aldose reductase gene The above disruptant cells may be constructed using known recombinant expression techniques. The disruption of ALD6 may be effected before, simultaneous or after any of the modifications 1)-5).

The yeast cell according to the invention may be subjected to evolutionary engineering to improve its properties. Evolutionary engineering processes are known processes. Evolutionary engineering is a process wherein industrially relevant phenotypes of a microorganism, herein the yeast, can be coupled to the specific growth rate and/or the affinity for a nutrient, by a process of rationally set-up natural selection. Evolutionary Engineering is for instance described in detail in Kuijper, M, et al, FEMS Yeast Research 5(2005) 925-934, WO2008041840 and WO2009112472. After the evolutionary engineering the resulting pentose fermenting yeast cell is isolated. The isolation may be executed in any known manner, e.g. by separation of cells from a yeast cell broth used in the evolutionary engineering, for instance by taking a cell sample or by filtration or centrifugation.

In an embodiment, the yeast cell is marker-free. As used herein, the term "marker" refers to a gene encoding a trait or a phenotype which permits the selection of, or the screening for, a host cell containing the marker. Marker-free means that markers are essentially absent in the yeast cell. Being marker-free is particularly advantageous when antibiotic markers have been used in construction of the yeast cell and are removed thereafter. Removal of markers may be done using any suitable prior art technique, e.g. intramolecular recombination.

In one embodiment, the industrial yeast cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

The yeast cell further may comprise those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a ß-lactam antibiotic or a cephalosporin.

In an embodiment, the yeast cell is derived from an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial yeast cell is constructed on the basis of an industrial host cell, wherein the construction is conducted as described hereinafter. Examples of industrial yeast (*S. cerevisiae*) are Ethanol Red® (Fermentis) Fermiol® (DSM) and Thermosacc® (Lallemand).

The yeast cells according to the invention are preferably inhibitor tolerant, i.e. they can withstand common inhibitors at the level that they typically have with common pretreatment and hydrolysis conditions, so that the yeast cells can find broad application, i.e. it has high applicability for different feedstock, different pretreatment methods and different hydrolysis conditions. In an embodiment the yeast cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

In an embodiment, the yeast cell is a cell that is naturally capable of alcoholic fermentation, preferably, anaerobic alcoholic fermentation. A yeast cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a yeast cell may be naturally present in the cell or may be introduced or modified by genetic modification.

Recombinant Expression

The yeast cell is a recombinant cell. That is to say, a yeast cell comprises, or is transformed with or is genetically modified with a nucleotide sequence that does not naturally occur in the cell in question.

Techniques for the recombinant expression of enzymes in a cell, as well as for the additional genetic modifications of a yeast cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i. e., a high acid-, ethanoland osmo-tolerance, capability of anaerobic growth, and of course its high alcoholic fermentative capacity. Preferred yeast species as host cells include *S. cerevisiae, S. bulderi, S. bametti, S. exiguus, S. uvarum, S. diastaticus, K. lactis, K. marxianus* or *K. fragilis*.

A yeast cell may be a cell suitable for the production of ethanol. A yeast cell may, however, be suitable for the production of fermentation products other than ethanol Such non-ethanolic fermentation products include in principle any bulk or fine chemical that is producible by a eukaryotic microorganism such as a yeast or a filamentous fungus.

A preferred yeast cell for production of non-ethanolic fermentation products is a host cell that contains a genetic modification that results in decreased alcohol dehydrogenase activity Lignocellulose Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes, The conversion with the cellulases may be executed at ambient temperatures or at higher temperatures, at a reaction time to release sufficient amounts of sugar(s). The result of the enzymatic hydrolysis is hydrolysis product comprising C5/C6 sugars, herein designated as the sugar composition.

The Sugar Composition

The sugar composition used according to the invention comprises glucose and one or more pentose, e.g. arabinose and/or xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocelllulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 10. The listed lignocelluloses include: corn cobs, corn fiber, rice hulls, melon shells, sugar beet pulp, wheat straw, sugar cane bagasse, wood, grass and olive pressings.

Table 10: Overview of sugar compositions from lignocellulosic materials. Gal=galactose, Xyl=xylose, Ara=arabinose, Man=mannose, Glu=glutamate, Rham=rhamnose. The percentage galactose (% Gal) is given.

| Lignocellulosic material | Gal | Xyl | Ara | Man | Glu | Rham | Sum | %. Gal. |
|---|---|---|---|---|---|---|---|---|
| Corn cob a | | 10 | 286 | 36 | | 227 | 11 | 570 | 1.7 |
| Corn cob b | | 131 | 228 | 160 | | 144 | | 663 | 19.8 |
| Rice hulls a | | 9 | 122 | 24 | 18 | 234 | 10 | 417 | 2.2 |
| Rice hulls b | | 8 | 120 | 28 | | 209 | 12 | 378 | 2.2 |

-continued

| Lignocellulosic material | Gal | Xyl | Ara | Man | Glu | Rham | Sum | %. Gal. |
|---|---|---|---|---|---|---|---|---|
| Melon Shells | 6 | 120 | 11 | | 208 | 16 | 361 | 1.7 |
| Sugar beet pulp | 51 | 17 | 209 | 11 | 211 | 24 | 523 | 9.8 |
| Whea straw Idaho | 15 | 249 | 36 | | 396 | | 696 | 2.2 |
| Corn fiber | 36 | 176 | 113 | | 372 | | 697 | 5.2 |
| Cane Bagasse | 14 | 180 | 24 | 5 | 391 | | 614 | 2.3 |
| Corn stover | 19 | 209 | 29 | | 370 | | 626 | |
| Athel (wood) | 5 | 118 | 7 | 3 | 493 | | 625 | 0.7 |
| Eucalyptus (wood) | 22 | 105 | 8 | 3 | 445 | | 583 | 3.8 |
| CWR (grass) | 8 | 165 | 33 | | 340 | | 546 | 1.4 |
| JTW (grass) | 7 | 169 | 28 | | 311 | | 515 | 1.3 |
| MSW | 4 | 24 | 5 | 20 | 440 | | 493 | 0.9 |
| Reed Canary Grass Veg | 16 | 117 | 30 | 6 | 209 | 1 | 379 | 4.2 |
| Reed Canary Grass Seed | 13 | 163 | 28 | 6 | 265 | 1 | 476 | 2.7 |
| Olive pressing residu | 15 | 111 | 24 | 8 | 329 | | 487 | 3.1 |

It is clear from table 10 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the yeast cell.

It is expected that yeast cells of the present invention can be further manipulated to achieve other desirable characteristics, or even higher overall ethanol yields.

Selection of improved yeast cells by passaging the yeast cells on medium containing hydrolysate has resulted in improved yeast with enhanced fermentation rates. Using the teachings of the present invention, one could readily such improved strains.

By pentose-containing material, it is meant any medium comprising pentose, whether liquid or solid. Suitable pentose-containing materials include hydrolysates of polysaccharide or lignocellulosic biomass such as corn hulls, wood, paper, agricultural biproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the yeast cell is able to grow under conditions similar to those found in industrial sources of pentose. The method of the present invention would be most economical when the pentose-containing material can be inoculated with the yeast variant without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of pentose in acid hydrolysates (or sulfite waste liquor) of hard woods and soft woods by the yeast cells of the present invention. It is reasonably expected that yeast strains capable of growing in sulfite waste liquor could grow be expected grow in virtually any other biomass hydrolysate.

Propagation

The invention further relates to a process for aerobic propagation of the acetate consuming yeast, in particular aerobic propagation of the disruptant yeast strain.

Propagation is herein any process of yeast growth that leads to increase of an initial yeast population. Main purpose of propagation is to increase a yeast population using the yeast's natural reproduction capabilities as living organisms. There may be other reasons for propagation, for instance, in case dry yeast is used, propagation is used to rehydrate and condition the yeast, before it is grown. Fresh yeast, whether active dried yeast or wet cake may be added to start the propagation directly.

The conditions of propagation are critical for optimal yeast production and subsequent fermentation, such as for example fermentation of lignocellulosic hydrolysate into ethanol. They include adequate carbon source, aeration, temperature and nutrient additions. Tank size for propagation and is normally between 2 percent and 5 percent of the (lignocellulosic hydrolysate to ethanol) fermentor size.

In the propagation the yeast needs a source of carbon. The source of carbon may herein comprise glycerol and/or acatete and or sugars (C6 and C5 sugars). Other carbon sources may also be used. The carbon source is needed for cell wall biosynthesis and protein and energy production.

Propagation is an aerobic process, thus the propagation tank must be properly aerated to maintain a certain level of dissolved oxygen. Adequate aeration is commonly achieved by air inductors installed on the piping going into the propagation tank that pull air into the propagation mix as the tank fills and during recirculation. The capacity for the propagation mix to retain dissolved oxygen is a function of the amount of air added and the consistency of the mix, which is why water is often added at a ratio of between 50:50 to 90:10 mash to water. "Thick" propagation mixes (80:20 mash-to-water ratio and higher) often require the addition of compressed air to make up for the lowered capacity for retaining dissolved oxygen. The amount of dissolved oxygen in the propagation mix is also a function of bubble size, so some ethanol plants add air through spargers that produce smaller bubbles compared to air inductors. Along with lower glucose, adequate aeration is important to promote aerobic respiration, which differs from the comparably anaerobic environment of fermentation. One sign of inadequate aeration or high glucose concentrations is increased ethanol production in the propagation tank.

Generally during propagation, yeast requires a comfortable temperature for growth and metabolism, for instance the temperature in the propagation reactor is between 25-40 degrees Celcius. Generally lower temperatures result in slower metabolism and reduced reproduction, while higher temperatures can cause production of stress compounds and reduced reproduction. In an embodiment the propagation tanks are indoors and protected from the insult of high summer or low winter temperatures, so that maintaining optimum temperatures of between within the range of 30-35 degrees C. is usually not a problem.

Further propagation may be conducted as propagation of yeast is normally conducted.

Fermentation

The yeast cell according to the invention is a pentose and glucose fermenting yeast cell that is capable of anaerobic simultaneous pentose and glucose consumption. Further the invention relates to a process for the fermentation of a yeast cell according to the invention, wherein the fermentation time for substantially complete fermentation of acetate, pentose and hexose is reduced relative to the corresponding fermentation of wild-type yeast. In an embodiment the fermentation time is reduced 40% or more. In a preferred fermentation process, pentose and glucose are co-fermented. In an embodiment of the process the overall ethanol production rate is at least about 20%, at least about 50% or about 100% higher than that of a process with the corresponding wild-type yeast. In an embodiment of the process the pentose-containing material comprises a hydrolysate of lignocellulosic material. The hydrolysate may be an enzymatic hydrolysate of lignocellulosic material.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/Uh, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, malic acid, fumaric acid, an amino acid and ethylene.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under microaerophilic or oxygen limited conditions.

An anaerobic fermentation process is herein defined as a fermentation process run in the absence of oxygen or in which substantially no oxygen is consumed, preferably less than about 5, about 2.5 or about 1 mmol/Uh, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 g/L-200 g/L, 40 g/L-200 g/L, 50 g/L-200 g/L, 60 g/L-200 g/L, 70 g/L-200 g/L, 80 g/L-200 g/L, 90 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose).

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180-0.511 gr ethanol/gr glucose.

For Butanol (MW 74 gr/mole) or iso butanol, the theoretical maximum yield is 1 mole of butanol per mole of glucose. So Yps max for (iso-)butanol=74/180-0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps g/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following non-limiting examples are intended to be purely illustrative.

EXAMPLES

Description of Mathematical Model

Description of Mathematical Model

A mathematical model description of xylose fermenting and glycerol acetate converting yeast strain was developed according to a minimal—model approach. A scheme of the lumped pathways included in the model is shown in FIG. 1. The following pathways are modeled: 1.) glucose uptake and metabolism (upper-glycolysis), 2.) xylose uptake and metabolism, 3.) glycerol uptake and metabolism, 4.) ethanol formation (lower glycolysis), 5.) acetate uptake and metabolism, 6.) biomass formation, 7.) ATP turnover for maintenance, 8.) C02 and ethanol production.

The mathematical equations used to model the biomass specific rates are:

glucose uptake $(g/gDW/\text{hour}) =$ $$V\max \times \frac{[\text{glucose}]}{[\text{glucose}] + KmGLC} \times \frac{[ATP]}{[ATP] + KmATP} \times \frac{1}{1 + \frac{[C\text{mol}]}{KiC\text{mol}}}$$

-continued xylose uptake $(g/gDW/\text{hour}) = V\max \times$ $$\frac{[xylose]}{[xylose] + \left(KmXYL \times \frac{[glucose]}{KiGLC}\right)} \times \frac{[ATP]}{[ATP] + KmATP} \times \frac{1}{1 + \frac{[Cmol]}{KiCmol}}$$

glycerol uptake $(g/gDW/\text{hour}) = V\max \times \frac{[glycerol]}{[glycerol] + KmGLY} \times$ $$\frac{[ATP]}{[ATP] + KmATP} \times \frac{[NAD]}{[NAD] + KmNAD} \times \frac{1}{1 + \frac{[glucose]}{KiGLC}}$$

acetate uptake $(g/gDW/\text{hour}) =$ $$V\max \times \frac{[acetate]}{[acetate] + KmACE} \times \frac{[ATP]}{[ATP] + KmATP} \times \frac{[NADH]}{[NADH] + KmNADH}$$

ethanol formation $(g/gDW/\text{hour}) =$ $$V\max \times \frac{[Cmol]^{nH}}{[Cmol]^{nH} + KmCmol^{nH}} \times \frac{[ADP]}{[ADP] + KmADP}$$

biomass formation $(g/gDW/\text{hour}) =$ $$V\max \times \frac{[Cmol]}{[Cmol] + KmCmol} \times \frac{[ATP]^{nH}}{[ATP]^{nH} + KmATP^{nH}}$$

maintenance $ATP(\text{mol}/gDW/\text{hour}) =$ $$k1 \times \frac{[ATP] - ATP_{LB}}{([ATP] - ATP_{LB}) + KmATP} \times \left(1 + k2 \times \frac{[acetate]^{nH}}{[acetate]^{nH} + KmACE^{nH}}\right)$$

$CO_2$ loss was calculated from the ethanol formation rate based on a 1:1 mol:mol ratio Unit conversion from g to Cmol was performed using the conversion factors listed in Table 11. ATP cost of biomass formation was set to 0.00675 mol ATP/gDW. NADH generation per biomass synthesis was set to 3e-3 mol/gDW.

TABLE 11 gram to Cmol unit conversion

| Metabolite | Molecular weight (g/mol) | Cmol/mol | Cmol/g |
|---|---|---|---|
| glucose | 180 | 6 | 0.033 |
| xylose | 150 | 5 | 0.033 |
| glycerol | 92 | 3 | 0.033 |
| acetate | 60 | 2 | 0.033 |
| ethanol | 46 | 2 | 0.043 |
| biomass | — | — | 0.037 |

Parameter values were estimated by minimizing the error between model predictions and time course data of sugars, ethanol, glycerol and acetate concentrations. The parameter values and initial conditions are listed in Table 12 and Table 13 respectively.

The model was implemented using MATLAB version R2012A (Mathworks) and ordinary differential equations were solved using a numerical ODE solver: ODE15s.

TABLE 12 parameter values used in mathematical model

| Glucose uptake | |
|---|---|
| Vmax | 0.975 (g/gDW/hour) |
| KmGLC | 0.5 (g/L) |
| KmATP | 1e−8 (mol/gDW) |
| KiCmol | 5e−6 (Cmol/gDW) |

TABLE 12-continued parameter values used in mathematical model

| Xylose uptake | |
|---|---|
| Vmax | 0.672 (g/gDW/hour) |
| KmXYL | 5 (g/L) |
| KiGLC | 10 (g/L) |
| KmATP | 1e−8 (mol/gDW) |
| KiCmol | 5e−6 (Cmol/gDW) |
| Glycerol uptake | |
| Vmax | 0.3 (g/gDW/hour) |
| KmGLY | 1 (g/L) |
| KmATP | 1e-7 (mol/gDW) |
| KmNAD | 1e−7 (mol/gDW) |
| KiGLC | 1e−3 (g/L) |
| Acetate uptake | |
| Vmax | 0.09 (g/gDW/hour) |
| KmACE | 2 (g/L) |
| KmATP | 1e−8 (mol/gDW) |
| KmNADH | 1e−7 (mol/gDW) |
| Ethanol formation | |
| Vmax | 20 (g/gDW/hour) |
| KmCmol | 1e−5 (Cmol/gDW) |
| nH | 2 (unitless) |
| KmADP | 1e−8 (mol/gDW) |
| Biomass formation | |
| Vmax | 2 g/gDW/hour |
| KmCmol | 1e−5 (Cmol/gDW) |
| KmATP | 1e−6 (mol/gDW) |
| nH | 1 (unitless) |
| Maintenance ATP | |
| k1 | 6e−3 (mol/gDW/hour) |
| $ATP_{LB}$ | 1e−8 (mol/gDW) |
| KmATP | 1e−8 (mol/gDW) |
| k2 | 14 (unitless) |
| nH | 2 (unitless) |
| KmACE | 15 (g/L) |

TABLE 131 initial conditions typical fermentation broth

| State variable | Initial condition |
|---|---|
| [glucose] | 42.3 (g/L) |
| [xylose] | 29.0 (g/L) |
| [acetate] | 3.6 (g/L) |
| [glycerol] | 10.6 (g/L) |
| [ethanol] | 0.5 (g/L) |
| [biomass] | 1.24 (gDW/L) |
| Intracellular [Cmol] | 5e−9 (Cmol/gDW) |
| Intracellular [ATP][#] | 5e−7 (mol/gDW) |
| Intracellular [NADH]* | 0 (mol/gDW) |
| Volume of fermenter | 1 (L) |

[#]intracellular [ADP] was calculated according to the relation: [ADP] (mol/gDW) = 1e−6 − ATP

*intracellular [NAD] was calculated according to the relation: [NAD] (mol/gDW) = 1e−6 − [NADH]

Materials and Methods

General Molecular Biology Techniques

Unless indicated otherwise, the methods used are standard biochemical techniques. Examples of suitable general methodology textbooks include Sambrook et al. [1] and Ausubel et al. [2].

Media

Liquid YEPhD medium (10 g/l yeast extract, 20 g/l phytone and 20 g/l glucose) was used for propagation and selection of transformants. To obtain solid medium, 15 g/l agar was added to the liquid medium before sterilization. Phleomycin was added to a final concentration of 60 µg/ml for selection of the zeoMX marker.

GAST medium was used as a pre-culture medium prior to the growth experiment (composition is shown in table 9). During the anaerobic growth experiment mineral medium was used as described by Verduyn et al [3], supplemented with histidine (200 mg/L), urea (2,325 g/l), ergosterol (0.01 g/l) and Tween80 (0.42 g/l). Sugars, glycerol and acetic acid were added as indicated.

TABLE 14

Composition of GAST medium

| Complete medium | g/kg | 1 | 0.25 |
|---|---|---|---|
| MES hydrate | 20 | 20 | 5 |
| K2HPO4 | 2 | 2 | 0.5 |
| NaH2PO4 · 1 aq | 1 | 1 | 0.25 |
| Yeast extract | 1 | 1 | 0.25 |
| Ammonium sulfate | 7.5 | 7.5 | 1.875 |
| Trace element solution TE-SF | 2 | 2 | 0.5 |
| Vitamin Ca Mg stock 100 × FS | 10 | 10 | 2.5 |
| pH with 4N KOH to pH 6 | | | |
| Starch (Zulkowsky) | 30 | 30 | 7.5 |
| Prepare in kg | | 1 | |

Dissolve all components except or starch, adjust pH, add starch and tilter-sterilize Glucoamylase (20-50 µl/L) was added just before starting the experiment Glucoamylase stock (HAS GLA for CGR contains 5000 GA/ml Pretreated corn stover hydrolysate was used as fermentation medium (composition is shown in table 10). Suspended solids in the hydrolysates were removed by centrifugation at 4520×g for 30 min, followed by filtration (106 µm) of the supernatant prior to fermentation. The pH of the medium was adjusted to 5.5 using ammonia, which also functioned as nitrogen source during growth. Both neomycin (50 ug/mL) and penicillin-G (100 ug/mL) were added to prevent bacterial contaminations during fermentation. Histidine was added (200 mg/mL) to complement the yeasts auxotrophy and silicone antifoam was added to prevent foaming in the fermentation flasks.

TABLE 15

Composition of pCS hydrolysate

| Compound | pCS hydrolysate (compounds g/l) |
|---|---|
| Sugar monomers: | |
| Glucose | 64.5 |
| Xylose | 33.6 |
| Arabinose | 4.1 |
| Inhibitors and byproducts: | |
| Acetic acid | 5.1 |
| Lactic acid | ND |
| Formic acid | 0.2 |
| Glycerol | 0.4 |
| Ethanol | ND |
| Hydroxymethylfurfural (HMF) | 0.4 |
| Furfural | 0.7 |

TABLE 15-continued

Composition of pCS hydrolysate

| Compound | pCS hydrolysate (compounds g/l) |
|---|---|
| Other analyses: | |
| pH | 4.5 |
| Dry Matter | 19.5% |
| Density | 1.05 g/ml |

Strains

Table 16 provides an overview of the strains that were used in these experiments. RN 1069 is a reference strain. It is a glucose, xylose converting strain which lacks the ability to consume glycerol and acetic acid under anaerobic conditions. YD01247 and YD01248 have been constructed by introducing the glycerol and acetic acid pathway genes in RN 1069, as is described in WO2015028583 and WO2015028582. From these patent applications, it is clear that the introduced genes differ between the two strains. YD01247 contains the bifunctional adhE gene from *E. coli* and the DAK1 gene from *Y. lypolitica*, whereas YD01248 contains the acdH gene from *L. plantarum* and an overexpression of DAK1 from *S. cerevisiae*.

TABLE 16

Used strains and their genetic background

| Strain | Background |
|---|---|
| RN1069 | HIS3::loxP, GPD1::hphMX, GPD2::natMX. xyIA, XKS1, TAL1, TKL1, RPE1 and RKI1 overexpression |
| YD01247 | RN1069 (INT1::pTDH3Ec.adhE-pENO1Ec.gldA-pPRE3ACS2-pTPI1Ylip.DAK1-G418R) |
| YD01248 | RN1069 (INT1::pTDH3Lpla.acdH-pENO1Ec.gldA-pPGK1ACS2- pTPI1DAK1-G418R) |

Integration Constructs and Selection of

Figure 2:
FIG. 2 shows a schematic overview of the approach: deletion of ALD6 using the zeoMX marker. These modifications were introduced in YD01247, YD01248.

The deletion of ALD6 was achieved using homologous recombination based on constructs shown in FIG. 2. FIG. 2 shows a schematic overview of the approach: deletion of ALD6 using the zeoMX marker. These modifications were introduced in YD01247, YD01248.

The zeoMX marker was used for selection.

After the transformation, correct integration was verified by PCR. Several independent transformants were picked. The transformant to be tested in AFM was selected based on performance in an anaerobic growth experiment.

Growth Experiment

Prior to the growth experiment, the transformants and reference strains were grown overnight at 30° C. on a YEPhD agarwell plate. The reference strains were plated in five-fold on the agarwell plate, whereas the independent transformants were plated in single-fold.

Liquid GAST medium pre-cultures were inoculated from the agarwell plate in 96 wells MTP format using a pintool. The pre-culture plates were incubated under aerobic conditions at 30° C., 250 rpm and 80% humidity in an Infors incubator for 72 hours.

Using a robotic inoculation unit, 5 µl of pre-culture was inoculated in the main culture plates. The following growth media were used in the main culture plates, 270 µl in each well:

Verduyn+2% glucose, 2% xylose, 2 g/l HAc, pH 4.5
Verduyn+2% glucose, 2% xylose, 1% glycerol, 2 g/l HAc, pH 4.5

One plate was prepared for each medium and each sample point (24, 48 and 72 hours), resulting in six main culture plates in total.

Main culture plates were incubated in an Infors shaking incubator at 30° C., 250 rpm, 80% humidity, the incubator was flushed with nitrogen to obtain (and retain) anaerobic conditions. Main culture plates were spun down after 24, 48 and 72 hours. 150 μl supernatant was added to a 96 deepwell plate containing 400 μl D20 in each well. 100 μl NMR standard (20 g/l maleic acid) was also added to each sample. For each sample residual sugars, glycerol, acetic acid and ethanol concentrations were determined using NMR analysis.

NMR Analysis

For the quantification of glucose, xylose, glycerol, acetic acid and ethanol in the sample, 100 μl sample was transferred accurately into a suitable vial. Subsequently 100 μl internal standard solution, containing maleic acid (20 g/l), EDTA (40 g/l) and trace amounts of DSS (4,4-dimethyl-4-silapentane-1-sulfonic acid) in D20, and 450 μL D20 was added.

1D $^1$H NMR spectra were recorded on a Bruker Avance III 700 MHz, equipped with a cryo-probe, using a pulse program with water suppression (power corresponding to 3 Hz) at a temperature of 27° C.

The analyte concentrations were calculated based on the following signals (5 relative to DSS):

α-glucose peak at 5.22 ppm (d, 0.38H, J=4 Hz),
α-xylose peak at 5.18 ppm (d, 0.37H, J=4 Hz),
glycerol peak at 3.55 ppm (dd, 2H, $J_{1,2}$=6 Hz and $J_{1a,1b}$=12 Hz)
acetic acid peak at 1.91 ppm (s, 3H)
ethanol peak at 1.17 ppm (t, 3H, J=7 Hz)
The signal used for the standard:
maleic acid peak at 6.05 ppm (s, 2H)

Yeast Cultivation for AFM Experiment

Strains, see table 5, were streaked on YEPhD agar plates from the corresponding glycerol stocks and the plates were incubated at 30° C. for 72 hours. A 200 mL mineral medium was inoculated using a streak of cells from the YEPhD agar plates. These pre-cultures were incubated overnight in a shaking incubator at 32° C. and 200 rpm. Cells were harvested by centrifugation and washed with ddH$_2$O. Cell pellets were then suspended in ddH$_2$O, using approximately ⅓th of the culture volume. Inoculum volume for the fermentation was calculated using the OD700 value of the yeast suspensions and a previously determined linear correlation between OD700 and yeast biomass.

The following strains were used during the AFM experiment:
1. YD01248 (reference)
2. YD01248 (ald6::loxPzeoMXloxP) col. #7
3. YD01247 (reference)
4. YD01247 (ald6::loxPzeoMXloxP) col. #2

AFM Conditions

The 500 mL fermentation flasks were filled with 400 mL hydrolysate and inoculated at a yeast biomass concentration of 0.5 g/L Fermentation medium was kept at 32° C. and stirred at 250 rpm, the pH was not controlled during fermentation. In addition to the online recording of CO$_2$ production by the AFM (correlating with ethanol (EtOH) and biomass formation), samples were taken with an interval frequency of 6 hours during the fermentation to monitor yeast growth-, substrate utilization- and product formation. Total fermentation time was 72 hours.

Example 1

Figure 3:
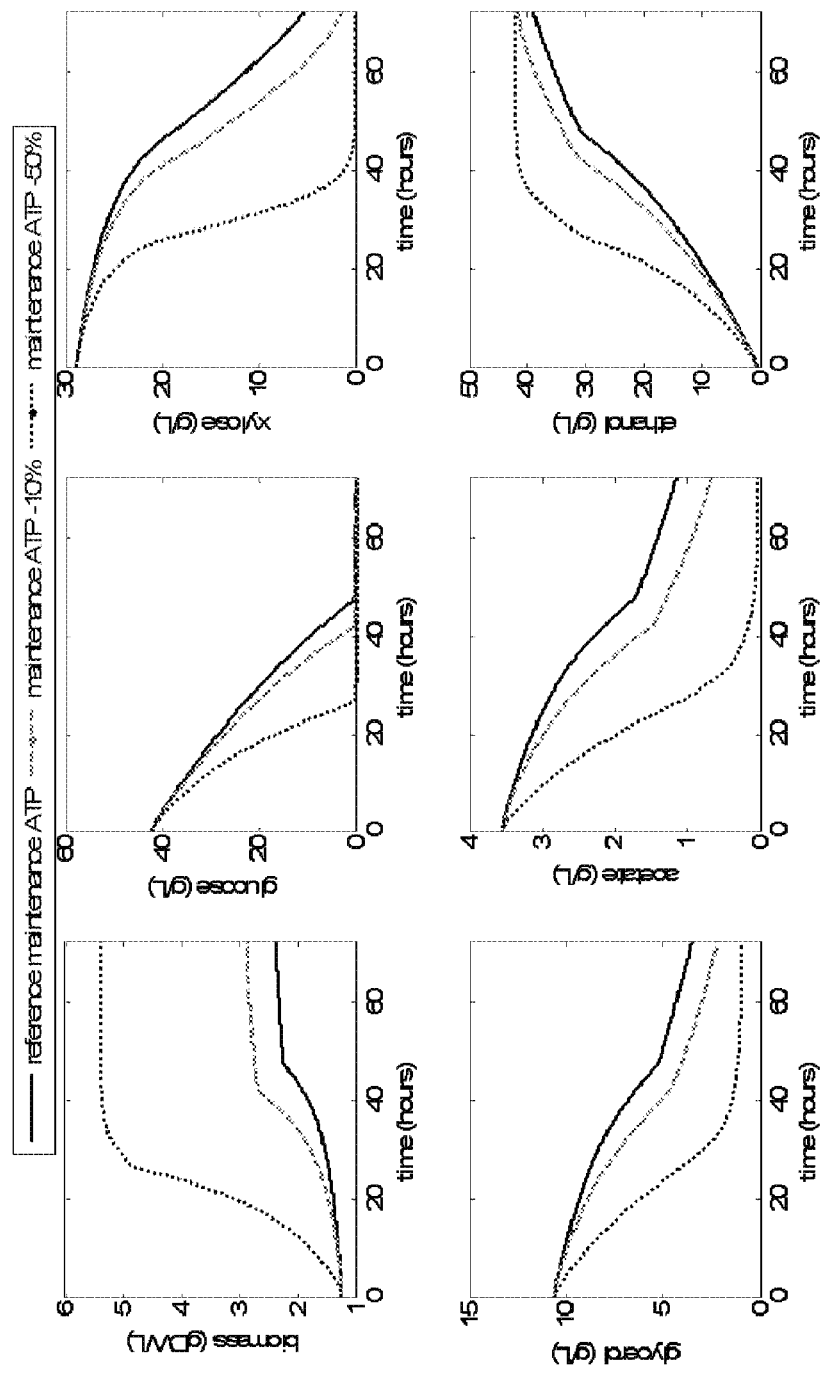
FIG. 3 shows model predictions of decreasing maintenance ATP on glucose and xylose to ethanol conversion rates.

Modeling Effect of Decreasing Maintenance ATP on Glucose and Xylose Conversion Rates Simulations with the mathematical model were performed to identify opportunities for improving the glucose and xylose conversion rates of glycerol and acetate converting yeast strains. The simulations indicated that high maintenance ATP demand of the cells delays xylose and glucose to ethanol conversions (see, FIG. 3). FIG. 3 shows predictions of the fermentation performance for a reference maintenance ATP demand (black lines), 10% decreased maintenance ATP demand (dashed grey lines) and 50% decreased maintenance ATP demand (dotted black lines). The 10% and 50% decrease in maintenance ATP was implemented by setting model parameter k1 (see, Table 2) to 5.4e-3 and 3e-3 (mol/gDW/hour), respectively. These results clearly show that the decreasing the maintenance ATP demand increases the rate of sugar to ethanol conversion. Even a small decrease in maintenance ATP (−10%) has already a significant effect.

Example 2

Identification of Disrupting Futile Cycle as Target for Decreased Maintenance ATP Demand The mathematical model predicted that decreasing the maintenance ATP demand will increase the sugar to ethanol conversion rates (see, Example 1). A possible source of maintenance ATP turnover is futile cycling. To enable acetate to ethanol conversion an acetylating acetaldehyde dehydrogenase (e.g., adhE or acdH) was introduced in the strains (see WO2015028583 and WO2015028583. This also introduced a possible futile cycle in the strains, see FIG. 4.

FIG. 3 shows a schematic overview of the metabolic pathways involved in futile cycling of acetaldehyde—acetate—acetyl-CoA, causing an increased maintenance ATP. The futile cycle is indicated by dotted arrows. The acetylating acetaldehyde dehydrogenase (adhE, acdH) was introduced in the strain to enable acetate to ethanol conversion.

Disruption of the futile cycle is expected to decrease the maintenance ATP and thereby improve the glucose and xylose to ethanol conversion (Example 1). The target for disruption of the futile cycle is the enzyme catalyzing the acetaldehyde to acetate conversion in the cytoplasm (ALD6). The ACS or acetylating acetaldehyde dehydrogenase cannot be a target for disrupting the futile cycle because these enzymes are part of the acetate to ethanol conversion pathway.

Example 3

AFM Test of ALD6 Knock-Out Strain

In order to experimentally verify the model predictions that ALD6 deletion increases the sugar to ethanol conversion rates the following strains were tested in AFM:
1. YD01248 (reference)
2. YD01248 (ald6::loxPzeoMXloxP) col. #7, herein "YD01248 ΔALD6"
3. YD01247 (reference)
4. YD01247 (ald6::loxPzeoMXloxP) col. #2, herein "YD01247ΔALD6"

Figure 5:
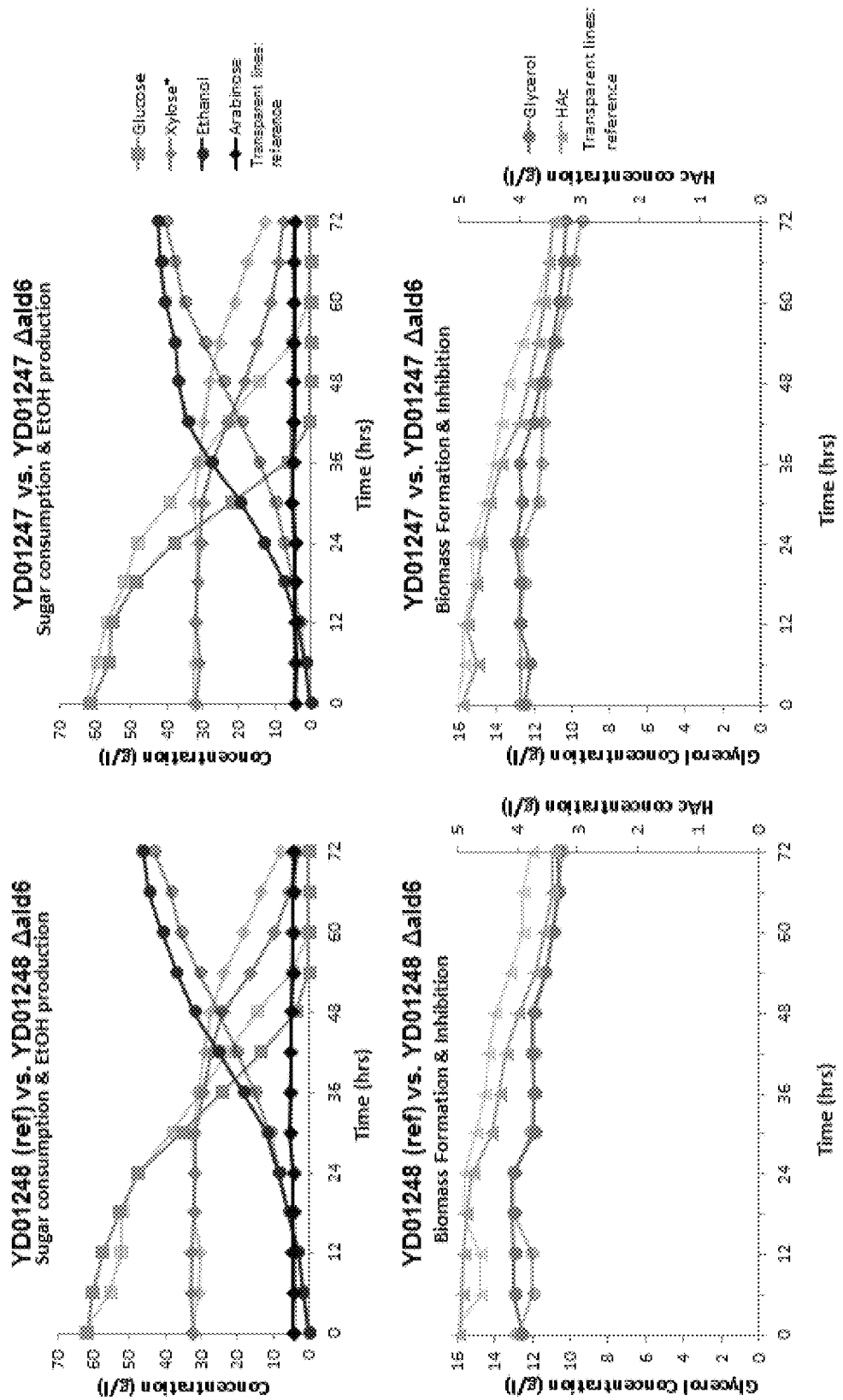
FIG. 5 shows a comparison of sugar consumption and ethanol formation rates between reference (YD01248, YD01247; transparent lines) and ALD6 deletion strains (YD01248Δald6, YD01247Δald6; solid lines).
Figure 5:
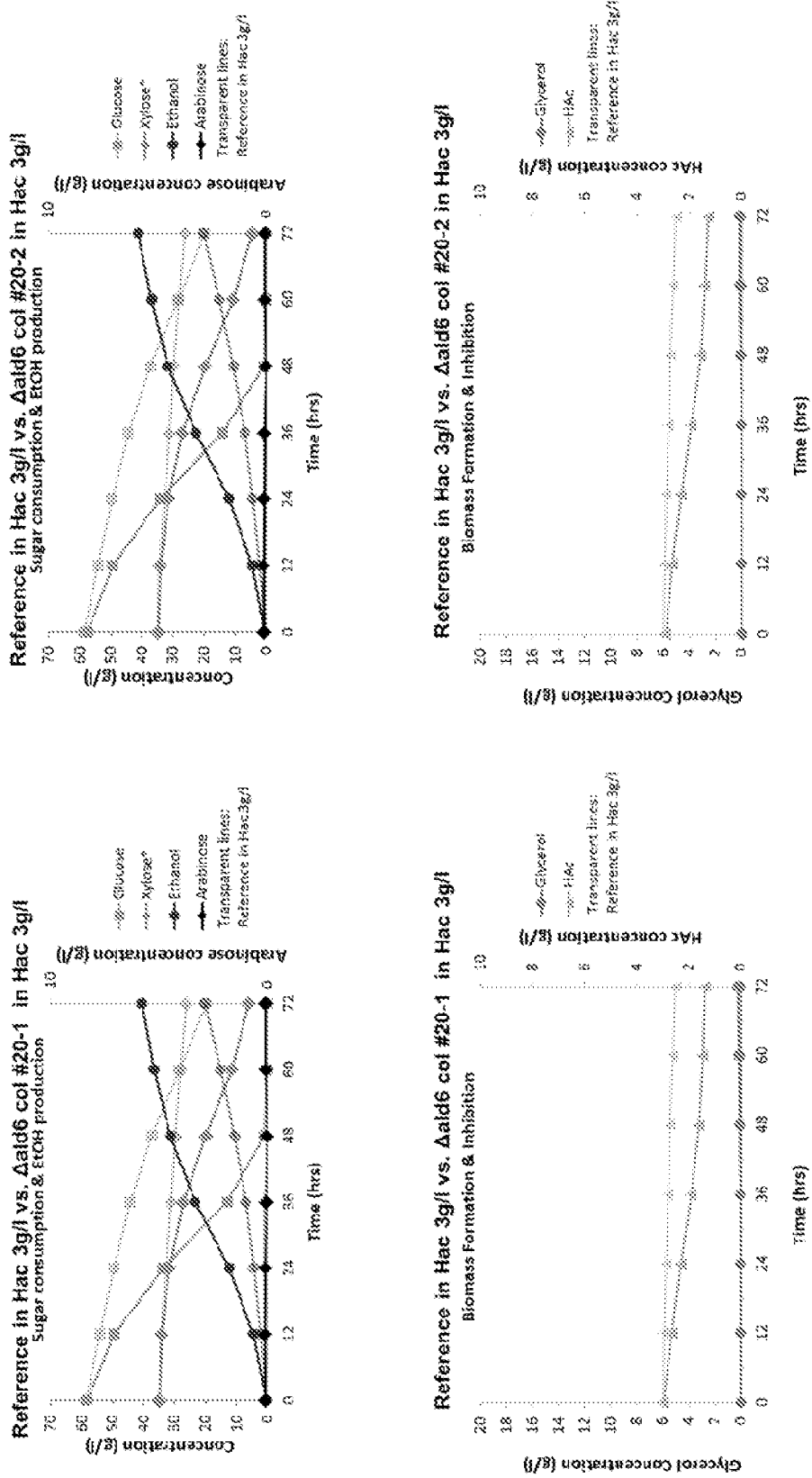
Figure 5:
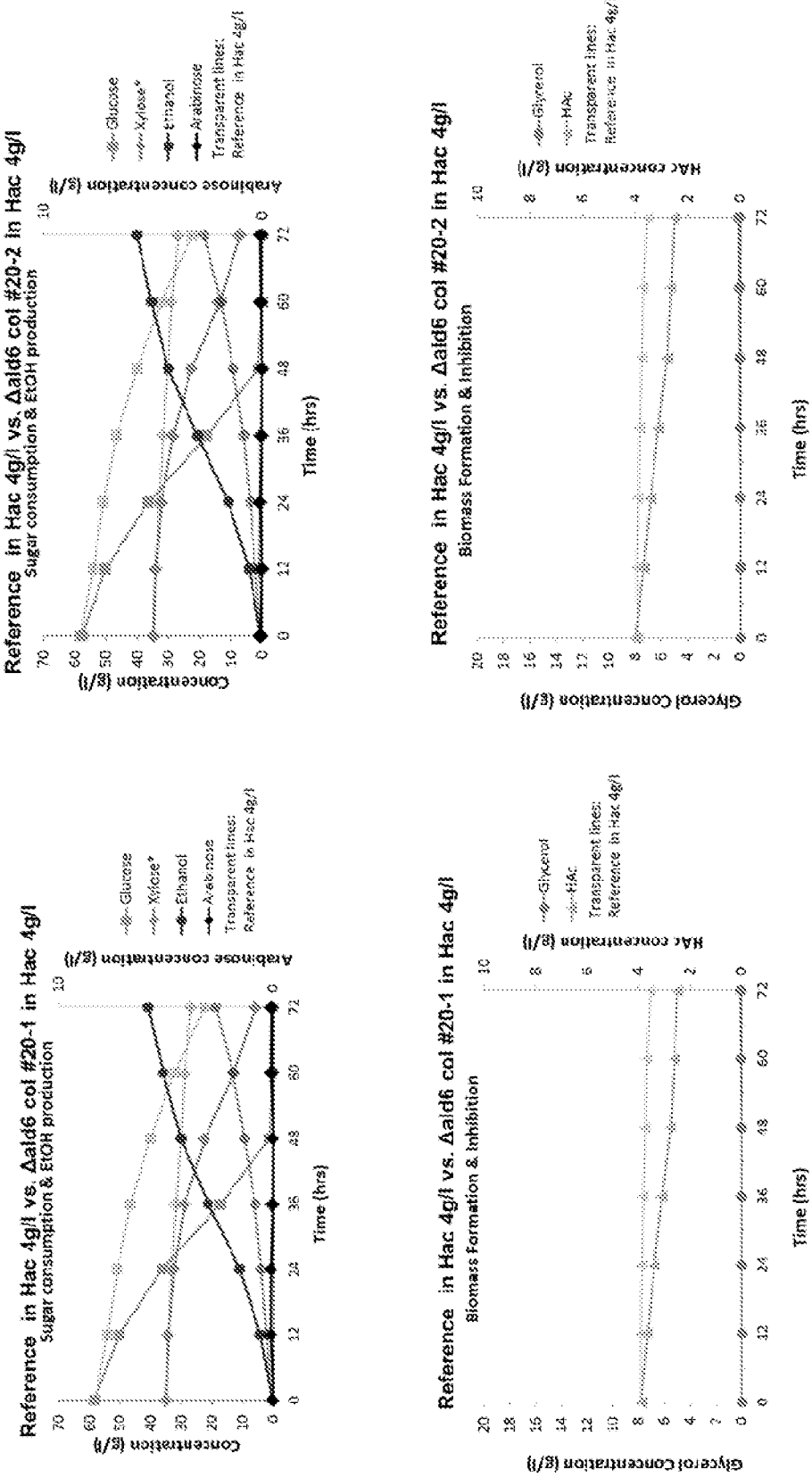

Every 6 hours, samples were taken for HPLC analysis, in order to determine the residual sugar concentration and the ethanol formation. The results are presented in FIG. 5. FIG. 5 shows a comparison of sugar consumption and ethanol formation rates between reference (YD01248, YD01247;

transparent lines) and ALD6 deletion strains (YD01248 ΔALD6, YD01247 ΔALD6; solid lines).

Table 12 summarizes the ethanol yields on total sugars for the reference vs. ALD6 deletion strains at 48 hours and 72 hours. FIG. 5 and Table 7 indicate that in both reference strains the ALD6 deletion resulted in increased sugar to ethanol conversion rates. These results confirm the model predictions and demonstrate the positive effect of ALD6 deletion on sugar to ethanol conversion in glycerol-acetate converting yeast strains.

TABLE 12

Ethanol yield on total sugars at 48 and 72 hours. Total sugars was defined as: glucose + xylose + arabinose at time is 0 hours.

| | Ethanol yield on total sugars at 48 hours (g/g) | Ethanol yield on total sugars at 72 hours (g/g) |
|---|---|---|
| YD01247 | 0.25 | 0.41 |
| YD01247 ΔALD6 | 0.38 | 0.44 |
| YD01248 | 0.25 | 0.43 |
| YD01248 ΔALD6 | 0.33 | 0.47 |

Example 4

AFM Test of ALD6 Knock-Out Strain in Absence of an Anaerobic Glycerol Fermentation Pathway (gldA, DAK1)

In order to experimentally verify to the benefits of ALD6 deletion in strains that do not contain the anaerobic glycerol fermentation pathway (gldA, DAK1) the following strains were constructed:

TABLE 13

| Strain | Genotype | Abbrevation |
|---|---|---|
| RN1069 + pRN595 | RN1069, pRN595 | Reference |
| RN1069-Δald6 + pRN595, #20-1 | RN1069; ald6::IoxP-kanMx-IoxP, pRN595, colony 20-1 | ΔALD6 #20-1 |
| RN1069-Δald6 + pRN595, #20-2 | RN1069; ald6::IoxP-kanMx-IoxP, pRN595, colony 20-2 | ΔALD6 #20-2 |

Table 13 provides an overview of the strains that were used in these experiments. Construction of RN1069 is described in WO2015028583. In summary, RN1069 is a histidine-auxotroph (his3 deletion) S. cerevisiae strain with introduced xylose fermentation pathway, and, additionally, gpd1 and gpd2 deleted. Therefore, RN1069 is unable to form biomass anaerobically since redox balance cannot be maintained due to the abbrogation of the glycerol formation pathway. RN1069 was transformed with pRN595. Construction of pRN595 was described in US2015176032. In summary, pRN595 is a high copy yeast expression vector, which bears the 2-micron origin of replication, HIS3 marker and the codon-optimized sequence of E. coli adhE under control of the S. cerevisiae PGK1 promoter. Correct transformants were selected based on selection on agar medium supplemented with 0.67 g/L yeast nitrogen base w/o amino acids (Sigma-Aldrich) and 2% v/v glucose without histidine added. Introduction of E. coli adhE in RN1069 allowed for growth anaerobically in the presence of acetic acid. One colony was selected and named RN1069+pRN595, which served as reference strain.

The deletion of ALD6 was achieved using homologous recombination similarly as described above. Deletion of ALD6 was accomplished by replacing the ORF by the kanMX marker. The floxed kanMX marker was PCR-amplified from plasmid pRN772 (SEQ ID NO: 1) using primers 12388+12389 (SEQ ID NO:2 and 3 respectively), which contained 50 bp homologous to the 5' sequence upstream of the ALD6 coding sequence and 50 bp homologous to the 3'sequence downstream to the ALD6 coding sequence, respectively. RN1069+pRN595 was transformed with the resulting PCR fragment and transformants were selected based on G418 resistance. After the transformation, correct integration of the kanMX marker at the ALD6 locus was verified by PCR. Two independent transformants were picked and their fermentation performance was tested in an AFM fermentation experiment.

The fermentations were performed on synthetic media mimicking the sugar constrations and acetate levels in pretreated corn stover hydrolysate. The media are based on standard Verduyn medium with urea as nitrogen source supplemented with 60 g/L glucose and 35 g/L xylose and acetic acid. Acetic acid was supplemented in two different initial concentrations: i.e., 3 g/L and 4 g/L. Starting pH of all media was set to pH=5.5. The 500 mL fermentation flasks were filled with 400 mL medium and inoculated at a yeast biomass concentration of 0.5 g/L. Fermentation medium was kept at 32° C. and stirred at 250 rpm, the pH was not controlled during fermentation. In addition to the online recording of C02 production by the AFM (correlating with ethanol (EtOH) and biomass formation), samples were taken with an interval frequency of 6 hours during the fermentation to monitor yeast growth-, substrate utilization- and product formation. Total fermentation time was 72 hours.

Every 6 hours, samples were taken for HPLC analysis, in order to determine the residual sugar concentration and the ethanol formation. The results are presented in FIGS. 6 and 7. FIGS. 6 and 7 show a comparison of sugar consumption and ethanol formation rates between reference and ald6 deletion strains for initial acetic acid concentration of 3 and 4 g/L, respectively. The reference is indicated with transparent lines and ALD6 deletion strains (Δald6) with solid lines.

Table 14 summarizes the ethanol yields on total sugars for the reference vs. ALD6 deletion strains at 48 hours and 72 hours. FIG. 6, 7 and Table 14 indicate that in both reference strains the ald6 deletion resulted in increased sugar to ethanol conversion rates.

TABLE 14

Ethanol yield on total sugars at 48 and 72 hours. Total sugars was defined as: glucose + xylose + arabinose at time is 0 hours.

| | Ethanol yield on total sugars at 48 hours (g/g) | Ethanol yield on total sugars at 72 hours (g/g) |
|---|---|---|
| Reference, Acetic acid 3 g/L | 0.11 | 0.21 |
| Δald6 #20-1, Acetic acid 3 g/L | 0.33 | 0.43 |
| Δald6 #20-2, Acetic acid 3 g/L | 0.34 | 0.44 |
| Reference, Acetic acid 4 g/L | 0.09 | 0.20 |
| Δald6 #20-1, Acetic acid 4 g/L | 0.32 | 0.43 |
| Δald6 #20-2, Acetic acid 4 g/L | 0.32 | 0.43 |

These results show that the ald6 deletion is also beneficial in strains without an anaerobic glycerol fermentation pathway (gldA, DAK1).

REFERENCES

1. Sambrook et al. (1989), "*Molecular Cloning, a laboratory manual*"
2. Ausubel et al. (1995), "*Current protocols in Molecular Biology*"
3. Verduyn et al. (1992) "*Effect of benzoic acid on metabolic fluxes in yeasts: a continuous culture study on the regulation of respiration and alcoholic fermentation*" Yeast 8: 501-517
4. Meaden et al. (1997), "*The ALD6 gene of Saccharomyces cerevisiae encodes a cytosolic, Mg(2+)-activated acetaldehyde dehydrogenase*", Yeast 13(14):1319-27
5. Saint-Prix et al. (2004), "*Functional analysis of the ALD gene family of Saccharomyces cerevisiae during anaerobic growth on glucose: the NADP+-dependent Ald6p and Ald5p isoforms play a major role in acetate formation*". Microbiology 150(Pt 7):2209-20

The invention claimed is:

1. A yeast cell that is genetically modified comprising:
   a) a disruption of one or more aldehyde dehydrogenase (E.C:1.2.1.4) native to the yeast;
   b) one or more nucleotide sequence encoding a heterologous NAD+-dependent acetylating acetaldehyde dehydrogenase (E.C. 1.2.1.10);
   c) one or more nucleotide sequence encoding a homologous or heterologous acetyl-CoA synthetase (E.C. 6.2.1.1); and
   d) a modification that leads to reduction of glycerol 3-phosphate phosphohydrolase (E.C. 3.1.3.21) and/or glycerol 3-phosphate dehydrogenase (E.C. 1.1.1.8 or E.C. 1.1.5.3) activity, native to the yeast.

2. The yeast cell according to claim 1, wherein the one or more aldehyde dehydrogenase (E.C:1.2.1.4) native to the yeast in a) is an acetaldehyde dehydrogenase-6 (ALD6).

3. The yeast cell according to claim 1, wherein the yeast cell comprises e) one or more nucleotide sequence encoding a heterologous xylose isomerase (E.C. 5.3.1.5).

4. The yeast cell according to claim 1, wherein the yeast cell comprises a disruption of one or more of the genes gpp1, gpp2, gpd1 and gpd2 native to the yeast.

5. The yeast cell according to claim 1, wherein the yeast cell comprises further:

f) one or more nucleotide sequence encoding a heterologous glycerol dehydrogenase (E.C. 1.1.1.6); and g) one or more nucleotide sequence encoding a homologous or heterologous dihydroxyacetone kinase (E.C. 2.7.1.28 or E.C. 2.7.1.29).

6. The yeast cell according to claim 1, wherein the yeast cell is a pentose and glucose fermenting yeast cell that is capable of anaerobic simultaneous pentose and glucose consumption.

7. A process for the fermentation of a yeast cell according to claim 1, wherein the fermentation time for substantially complete fermentation of acetate, pentose and hexose is reduced relative to the corresponding fermentation of wild-type yeast.

8. The process according to claim 7, wherein the fermentation time is reduced 40% or more.

9. The process according to claim 6, wherein pentose and glucose are co-fermented.

10. The process according to any of claim 7, wherein the overall ethanol production rate is at least about 20%, at least about 50% or about 100% higher than that of a process with the corresponding wild-type yeast.

11. The process according to claim 7, wherein a hydrolysate of lignocellulosic material is fermented.

12. The process according to claim 11, wherein the hydrolysate is an enzymatic hydrolysate of lignocellulosic material.

13. The process according to claim 11, wherein the hydrolysate comprises acetate.

14. The process according to claim 13, wherein the acetate comprising hydrolysate has an acetate concentration of 5% (w/w) or more.

* * * * *